(12) United States Patent
Baniecki et al.

(10) Patent No.: US 12,209,292 B2
(45) Date of Patent: Jan. 28, 2025

(54) NUCLEIC ACID AMPLIFICATION ASSAYS FOR DETECTION OF PATHOGENS

(71) Applicants: THE BROAD INSTITUTE, INC., Cambridge, MA (US); MASSACHUSETTS INSTITUTE OF TECHNOLOGY, Cambridge, MA (US); PRESIDENT AND FELLOWS OF HARVARD COLLEGE, Cambridge, MA (US)

(72) Inventors: Mary Lynn Baniecki, Cambridge, MA (US); Hayden Metsky, Cambridge, MA (US); Pardis Sabeti, Cambridge, MA (US)

(73) Assignees: The Broad Institute, Inc., Cambridge, MA (US); Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 1101 days.

(21) Appl. No.: 16/328,548

(22) PCT Filed: Aug. 25, 2017

(86) PCT No.: PCT/US2017/048744
§ 371 (c)(1),
(2) Date: Feb. 26, 2019

(87) PCT Pub. No.: WO2018/039640
PCT Pub. Date: Mar. 1, 2018

(65) Prior Publication Data
US 2019/0194766 A1 Jun. 27, 2019

Related U.S. Application Data

(60) Provisional application No. 62/380,353, filed on Aug. 26, 2016.

(51) Int. Cl.
| | | |
|---|---|---|
| *C12Q 1/68* | (2018.01) | |
| *C12Q 1/6893* | (2018.01) | |
| *C12Q 1/70* | (2006.01) | |
| *G16B 30/00* | (2019.01) | |
| *G16B 30/10* | (2019.01) | |

(52) U.S. Cl.
CPC ........... *C12Q 1/702* (2013.01); *C12Q 1/6893* (2013.01); *C12Q 1/701* (2013.01); *G16B 30/00* (2019.02); *C12Q 2600/158* (2013.01); *G16B 30/10* (2019.02)

(58) Field of Classification Search
None
See application file for complete search history.

(56) References Cited

U.S. PATENT DOCUMENTS

| | | |
|---|---|---|
| 5,427,930 A | 6/1995 | Birkenmeyer et al. |
| 5,445,934 A | 8/1995 | Fodor et al. |
| 5,541,308 A * | 7/1996 | Hogan .................. C12Q 1/689 |
| | | 435/6.12 |
| 5,744,311 A | 4/1998 | Fraiser et al. |
| 6,025,134 A | 2/2000 | Sooknanan |
| 6,027,889 A | 2/2000 | Barany et al. |
| 6,033,881 A | 3/2000 | Himmler et al. |
| 8,999,675 B2 | 4/2015 | Carrick et al. |
| 2009/0105092 A1* | 4/2009 | Lipkin .................. G16B 50/00 |
| | | 435/5 |
| 2013/0230857 A1 | 9/2013 | Gnirke et al. |
| 2013/0267429 A1 | 10/2013 | Gardner et al. |
| 2015/0275204 A1 | 10/2015 | Iverson et al. |

FOREIGN PATENT DOCUMENTS

| | | |
|---|---|---|
| WO | 90/01069 A1 | 2/1990 |
| WO | 2008101142 A1 | 8/2008 |
| WO | 2014/047556 A1 | 3/2014 |
| WO | 2016112188 A1 | 7/2016 |
| WO | 2018039640 A1 | 3/2018 |
| WO | 2018039640 A9 | 12/2018 |

OTHER PUBLICATIONS

Stephens et al; Molecular and Cellular Probes, vol. 24, 2010, pp. 370-375.*
Sanchez and Rollin, Viral Research, vol. 113, pp. 16-25, 2005.*
Accession No. KR006950 (NCBI, NLM, Mar. 30, 2015).*
Buck et al; Biotechniques (1999) 27(3):528-536.*
"International Search Report and Written Opinion", ISR/WO issued in PCT Application No. PCT/US2017/048744 mailed Nov. 17, 2017, 1-14.
Jabado, et al., "Comprehensive Viral Oligonucleotide Probe Design Using Conserved Protein Regions", Nucleic Acids Research, vol. 36, No. 1, Dec. 13, 2007, 10.
The Broad Institute, Inc., "International Preliminary Report on Patentability issued in International Patent Application No. PCT/US2017/048744", mailed on Mar. 7, 2019, 11 pages.
Atschul, et al., "Basic Local Alignment Search Tool", Journal of Molecular Biology, vol. 215, 1990, 403-410.

(Continued)

*Primary Examiner* — Jehanne S Sitton
(74) *Attorney, Agent, or Firm* — F. Brent Nix, Esq.; Johnson, Marcou, Isaacs & Nix, LLC; Erin M. Daly

(57) ABSTRACT

The present invention relates to a method for generating primers and/or probes for use in analyzing a sample which may comprise a pathogen target sequence comprising providing a set of input genomic sequence to one or more target pathogens, generating a set of target sequences from the set of input genomic sequences, identifying one or more highly conserved target sequences, and generating one or more primers, one or more probes, or a primer pair and probe combination based on the one or more conserved target sequences.

1 Claim, 15 Drawing Sheets

Specification includes a Sequence Listing.

(56) References Cited

OTHER PUBLICATIONS

Corpet, Florence "Multiple Sequence Alignment with Hierarchical Clustering", Nucleic Acids Research, vol. 16, No. 22, 1988, 10881-10890.

Devereux, et al., "A Comprehensive Set of Sequence Analysis Programs for the VAX", Nucleic Acids Research, vol. 12, No. 1, 1984, 387-395.

Duitama, et al., "PrimerHunter: A Primer Design Tool for PCR-Based Virus Subtype Identification", Nucleic Acids Research, vol. 37, No. 8, May 2009, 14 pages.

Empedocles, et al., "Three-Dimensional Orientation Measurements of Symmetric Single Chromophores using Polarization Microscopy", Nature, vol. 399, Issue 6732, May 13, 1999, 126-130.

Gire, et al., "Genomic Surveillance Elucidates Ebola Virus Origin and Transmission During The 2014 Outbreak", Science, vol. 345, No. 6202, Sep. 12, 2014, 11 pages.

Higgins, et al., "CLUSTAL: A Package for Performing Multiple Sequence Alignment on a Microcomputer", Gene, vol. 73, No. 2, 1988, 237-244.

Higgins, et al., "Fast and Sensitive Multiple Sequence Alignments on a Microcomputer", CABIOS Communications, vol. 5, No. 2, 1989, 151-153.

Huang, et al., "Parallelization of a Local Similarity Algorithm", Computer Applications in the Biosciences, vol. 8, No. 2, 1992, 155-165.

Jabado, et al., "Greene SCPrimer: A Rapid Comprehensive Tool for Designing Degenerate Primers from Multiple Sequence Alignments", Nucleic Acids Research, vol. 34, No. 22, 2006, 6605-6611.

Needleman, et al., "A General Method Applicable to the Search for Similarities in the Amino Acid Sequence of Two Proteins", Journal of Molecular Biology, vol. 48, No. 3, 1970, 443-453.

Pearson, et al., "Improved Tools for Biological Sequence Comparison", Proc. Natl. Acad. Sci. USA, vol. 85, Apr. 1988, 2444-2448.

Pearson, et al., "On the Primer Selection Problem in Polymerase Chain Reaction Experiments", Discrete Applied Mathematics, vol. 71, Issue(1-3), Jul. 12, 1996, 231-246.

Pearson, et al., "Using the FASTA Program to Search Protein and DNA Sequence Databases", Methods in Molecular Biology, vol. 24, Chapter 26, 1994, 307-331.

Phillippy, et al., "Efficient Oligonucleotide Probe Selection for Pan-Genomic Tiling Arrays", BMC Bioinformatics, vol. 10, No. 293, Sep. 16, 2009, 14 pages.

Reichert, et al., "Chip-Based Optical Detection of DNA Hybridization by Means of Nanobead Labeling", Analytical Chemistry, vol. 72, No. 24, Nov. 14, 2000, 6025-6029.

Smith, et al., "Comparison of Biosequences", Advances in Applied Mathematics, vol. 2, 1981, 482-489.

Tatusova, et al., "BLAST 2 Sequences, A New Tool for Comparing Protein and Nucleotide Sequences", FEMS Microbiology Letters, vol. 174, Issue 2, 1999, 247-250.

Tatusova, et al., "Erratum to "BLAST 2 Sequences, A New Tool for Comparing Protein and Nucleotide Sequences"", FEMS Microbiology Letters, vol. 177, Issue 1, 1999, 187-188.

* cited by examiner

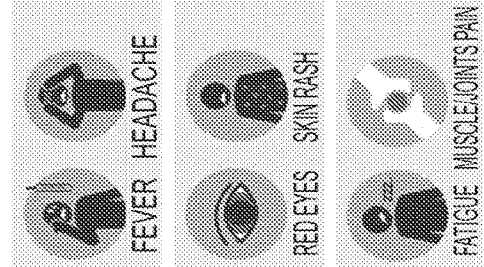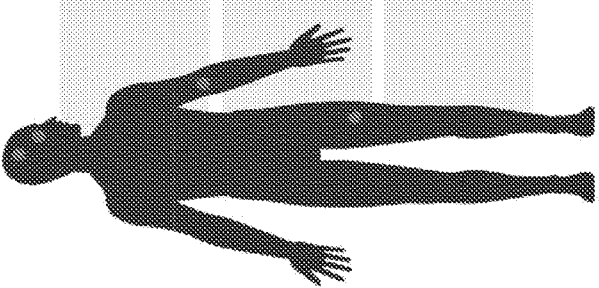
FIG. 3

| Assay | Target | No. potential nucleotide mismatches* | Forward primer sequence (5' → 3') | Probe sequence (5' → 3')§ | Reverse primer sequence (5' → 3') | Reported sensitivity (copies/ul) |
|---|---|---|---|---|---|---|
| Lanciotti M (2008) | M | 3 | TTGGTCATGATACTGCTGATTGC | CGGCATACAGCATCAGGTGCATAGGAG | CCTTCCACAAGTCCCTATTGC | 3.2 |
| Lanciotti E (2008) | E | 2 | TCGCTGCCCAACACAAG | AGCCTACCTTGACAAGCAGTCAGACACTCAA | CCACTAATGTTCTTTTGCAGACAT | 4.1 |
| Balm NS5 (2012) | NS5 | N/A | CTTGGATTCTTGAACGA | N/A – amplicons visualized on gel | GAGCTTCATTCTCCAGATCA | 28 |
| Tappe NS3 (2013) | NS3 | 4 | GAGATGAGTACATGTA | CTGATGAAGgCCATGCACACTG | GGTAGATGTTGTCAAGATTGTCAAGA | 1,377.3 |
| Faye NS5 (2013) | NS5 | 2 | AARTACACATACCARAAACAAAGTGGT | CTCAGACCAGCTGAAG | TCCRCTCCCYCTYGGTGGTCTTG | 4.5 |
| Pyke E (2014) | E | 6 | AAGTTTGCATGCTCCAAGAAAAT | ACCGGGAAGAGCATCCAGCCAGA | CAGCATTATCCGGTACTCCAGAT | 5.3 |
| Pyke NS1 (2014) | NS1 | 7 | GCACAATGCCCCCACTGT | TTCCGGGCTAAGATGCTGITGGT | TGGGCCTTATCTCCATTCCA | 12.1 |

Africa: Lanciotti M (2008), Lanciotti E (2008), Balm NS5 (2012), Tappe NS3 (2013), Faye NS5 (2013)
Asia: Pyke E (2014), Pyke NS1 (2014)

Degenerate bases underlined

FIG. 6

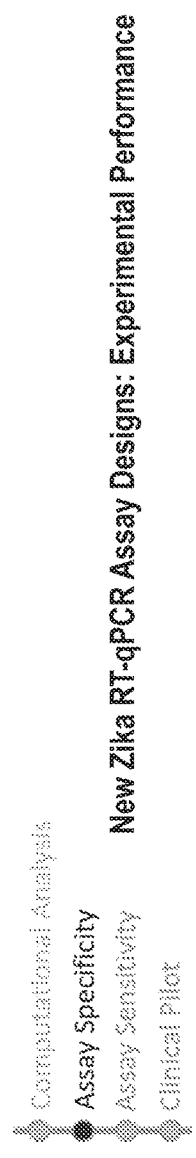
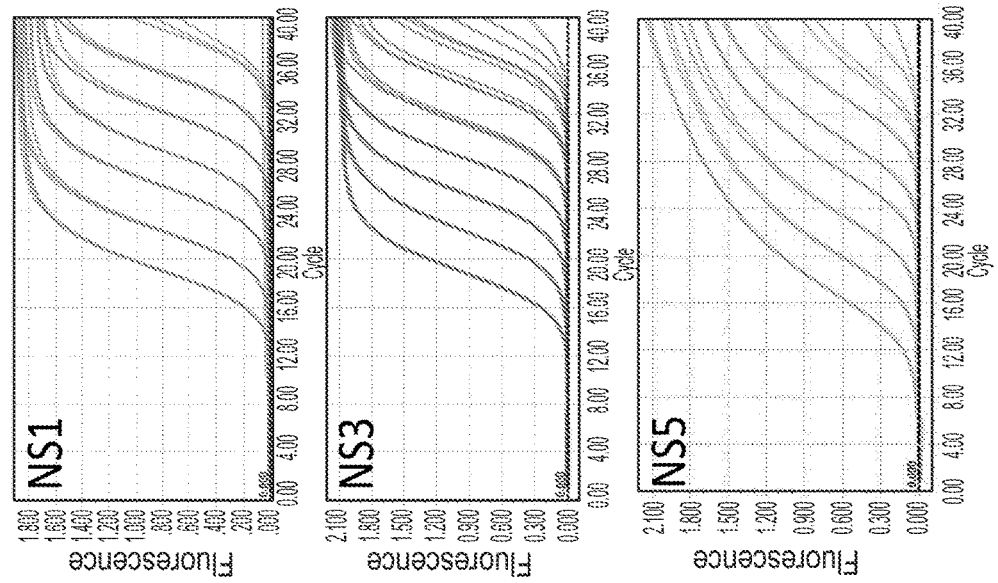
New Zika RT-qPCR Assay Designs: Experimental Performance
| copies/µl | Pyke (E) Cq Mean | New (NS1) Cq Mean | New (NS2) Cq Mean | New (NS5) Cq Mean |
|---|---|---|---|---|
| 1.00E+07 | 11.75 ± 0.09 | 14.59 ± 0.03 | 13.94 ± 0.09 | 9.96 ± 0.05 |
| 1.00E+06 | 15.17 ± 0.08 | 18.35 ± 0.04 | 16.70 ± 0.11 | 14.04 ± 0.15 |
| 1.00E+05 | 18.18 ± 0.58 | 21.91 ± 0.04 | 19.97 ± 0.06 | 17.85 ± 0.11 |
| 1.00E+04 | 21.71 ± 0.08 | 25.01 ± 0.07 | 23.03 ± 0.04 | 21.73 ± 0.06 |
| 1.00E+03 | 25.58 ± 0.11 | 28.11 ± 0.05 | 26.02 ± 0.19 | 24.72 ± 0.17 |
| 1.00E+02 | 28.69 ± 0.11 | 31.08 ± 0.17 | 29.52 ± 0.29 | 28.24 ± 0.20 |
| 1.00E+01 | 33.41 ± 0.93 | 35.32 ± 0.45 | 32.25 ± 0.38 | 31.01 ± 0.54 |
| 1.00E+00 | 36.04 ± 0.03 | 35.80 ± 0.13 | 33.97 ± 0.00 | 34.11 ± 0.00 |
| NTC | - | - | - | - |
| Efficiency | 1.92 ± 0.53 | 2.17 ± 0.77 | 2.08 ± 0.6 | 1.94 ± 0.53 |
FIG. 11

Computational Analysis
Assay Specificity
Assay Sensitivity
Clinical Pilot

New NS5 Diagnostic Detects Zika Virus at Low Viral Titer

- Our new Zika probe-based diagnostic has greater specificity and sensitivity then the published gold standard diagnostics eliminating:
  - False positive diagnosis by SYBR-based detection
  - False negative diagnosis by Probe-based detection*
- Our Zika WGS method is very sensitive detecting Zika virus as low as 200 copies with over 90% genome coverage.**

| | "Gold Standard" Published Diagnostics | | In-House Zika Diagnostic | | In-House Zika Whole Genome Sequence (WGS) |
|---|---|---|---|---|---|
| Sample ID | Faye et al. SYBR- Based | Pyke et al. Probe-Based | In-House (NS5) Probe-Based | Quantity of Zika (Copies) | % Coverage (Illulmina HiSeq) |
| Brazil-1 | + | - | - | 0 | 0 |
| Brazil-2 | + | + | + | 101 | 0 |
| Brazil-3 | + | - | - | 0 | 0 |
| Brazil-4 | + | + | + | 201 | 92** |
| Brazil-5 | + | - | + | 851 | 96 |
| Brazil-6 | + | - | + | 23* | 0 |
| Brazil-7 | + | - | - | 0 | 0 |
| Brazil-8 | + | + | + | 940 | 93 |
| Brazil-9 | + | - | - | 0 | 0 |
| Brazil-10 | + | - | - | 0 | 0 |
| Brazil-11 | + | - | + | 30* | 0 |
| Brazil-12 | + | - | + | 35* | 0 |
| Brazil-13 | + | - | - | 0 | 0 |
| Brazil-14 | + | + | + | 5397 | 97 |
| Brazil-15 | + | - | - | 0 | 0 |
| Brazil-16 | + | - | - | 0 | 0 |

FIG. 15

| | Forward Primer | Probe | Reverse Primer |
|---|---|---|---|
| New NS1 | ATTGAGGAATGGTGCTGTAGG | AAGACGGCTGCTGGTATGGAATGG | AGATAAGGCCCAGGAAAGAAC |
| Asia | ATTGAGGAATGGTGCTGTAGG | AAGACGGCTGCTGGTATGGAATGG | AGATAAGGCCCAGGAAAGAAC |
| Africa | ATTGAGGAATGGTGCTGTAGG | AAGACGGCTGCTGGTATGGAATGG | AGATAAGGCCCAGGAAGGAAC |
| South America | ATTGAGGAATGGTGCTGTAGG | AAGACGGCTGCTGGTATGGAATGG | AGATAAGGCCCAGGAAAGAAC |
| | | | |
| New NS3 | GGCTTGAAGCAAGAATGCTT | AGATGGCCTCATAGCCTGCTCTA | AAAGTAGCCATTGAGGG |
| Asia | GGCTTGAAGCAAGAATGCTT | AGATGGCCTCATAGCCTCGCTCTA | AAAGTAGCAGCGCCATTGAGGG |
| Africa | GGCTTGAAGCAAGAATGCTT | GATGGCCTCATAGCCTCGCTCTA | AAAGTAGCCATTGAGGG |
| South America | GGCTTGAAGAGAATGCTC | AGATGGCCTCATAGCCTCGCTCTA | AAAGTAGCCATTGAGGG |
| | | | |
| New NS5 | TCATGAAGAACCATGTTGG | TGCAAAGCTATGGTGGAACA | TCTTTCATGGCTGAG |
| Asia | TCATGAAGAACCATGTTGG | TGCAAAGCTATGGTGGAACA | TCTTTCACATGGGCGGCTGAG |
| Africa | TCATGAAGAACCATGCTGG | TGCAAAGCTATGGTGGAACA | TCTTTCCACATGGGCGGCTGAG |
| South America | TCATGAAGAACCCRTGTTGG | TGCAAAGCTATGGTGGAACA | TCTTTCATGGGCGGCTGAG |
| | | | |
| New NS1 (Multiplex) | TSYACGGARTGCACAAT | TGTTATGAATGGAGATAAGGCCC | RAARGAACCAGARGAACTTAGT |
| Asia | TCCAGGGARTGCACAAT | TGGTATGGAATGGAGATAAGGCCC | RAAAGAACCAGAAAGYAACTTAGT |
| Africa | TGTAGGGAATGCACAAT | TGGTATGGAATGGAGATAAGGCCC | RAARGAACCAGARGCAACTTAGT |
| South America | TGCAGGGAGTGCACAAT | TGGTATGGAATGGAGATAAGGCCC | GAAAGAACCAGAAAGYAACTTAGT |

SEQUENCE LISTING

<160> NUMBER OF SEQ ID NOS: 58

<210> SEQ ID NO 1
<211> LENGTH: 19
<212> TYPE: DNA
<213> ORGANISM: Ebola virus

<400> SEQUENCE: 1
aatcgagcgc aaggttaca                                          19

<210> SEQ ID NO 2
<211> LENGTH: 21
<212> TYPE: DNA
<213> ORGANISM: Ebola virus

<400> SEQUENCE: 2
cttgcttggt gtctggagta t                                       21

<210> SEQ ID NO 3
<211> LENGTH: 28
<212> TYPE: DNA
<213> ORGANISM: Ebola virus

<400> SEQUENCE: 3
aggttgaact gagagtgtct agacaaca                                28

```
<210> SEQ ID NO 4
<211> LENGTH: 76
<212> TYPE: DNA
<213> ORGANISM: Ebola virus

<400> SEQUENCE: 4
aatcgagcgc aaggttacaa ggttgaactg agagtgtcta gacaacaaaa tatcgatact    60
ccagacacca agcaag                                                   76

<210> SEQ ID NO 5
<211> LENGTH: 20
<212> TYPE: DNA
<213> ORGANISM: Zika virus

<400> SEQUENCE: 5
ggcttgaagc aagaatgctc                                               20

<210> SEQ ID NO 6
<211> LENGTH: 20
<212> TYPE: DNA
<213> ORGANISM: Zika virus

<400> SEQUENCE: 6
ccctcaatgg ctgctacttt                                               20

<210> SEQ ID NO 7
<211> LENGTH: 24
<212> TYPE: DNA
<213> ORGANISM: Zika virus

<400> SEQUENCE: 7
agatggcctc atagcctcgc tcta                                          24

<210> SEQ ID NO 8
<211> LENGTH: 100
<212> TYPE: DNA
<213> ORGANISM: Zika virus

<400> SEQUENCE: 8
ggcttgaagc aagaatgctc cttgacaata tttacctcca agatggcctc atagcctcgc   60
tctatcgacc tgaggccgac aaagtagcag ccattgaggg                         100

<210> SEQ ID NO 9
<211> LENGTH: 21
<212> TYPE: DNA
<213> ORGANISM: Zika virus

<400> SEQUENCE: 9
attgaggaat ggtgctgtag g                                             21

<210> SEQ ID NO 10
<211> LENGTH: 21
<212> TYPE: DNA
<213> ORGANISM: Zika virus

<400> SEQUENCE: 10
gttctttcct gggccttatc t                                             21

<210> SEQ ID NO 11
<211> LENGTH: 24
<212> TYPE: DNA
<213> ORGANISM: Zika virus
```

```
<400> SEQUENCE: 11
aagacggctg ctggtatgga atgg                                          24

<210> SEQ ID NO 12
<211> LENGTH: 100
<212> TYPE: DNA
<213> ORGANISM: Zika virus

<400> SEQUENCE: 12
attgaggaat ggtgctgtag ggaatgcaca atgcccccac tatcgtttcg agcaaaagac   60
ggctgctggt atggaatgga gataaggccc aggaaagaac                        100

<210> SEQ ID NO 13
<211> LENGTH: 20
<212> TYPE: DNA
<213> ORGANISM: Zika virus

<400> SEQUENCE: 13
tcatgaagaa cccrtgytgg                                               20

<210> SEQ ID NO 14
<211> LENGTH: 20
<212> TYPE: DNA
<213> ORGANISM: Zika virus

<400> SEQUENCE: 14
ctcagccgcc atrtgraaga                                               20

<210> SEQ ID NO 15
<211> LENGTH: 21
<212> TYPE: DNA
<213> ORGANISM: Zika virus

<400> SEQUENCE: 15
tgcaaagcta tgggtggaac a                                             21

<210> SEQ ID NO 16
<211> LENGTH: 21
<212> TYPE: DNA
<213> ORGANISM: Zika virus

<400> SEQUENCE: 16
tgcaaagcta tgggtggaac a                                             21

<210> SEQ ID NO 17
<211> LENGTH: 20
<212> TYPE: DNA
<213> ORGANISM: Zika virus

<400> SEQUENCE: 17
agyygaytgg gthccaactg                                               20

<210> SEQ ID NO 18
<211> LENGTH: 22
<212> TYPE: DNA
<213> ORGANISM: Zika virus

<400> SEQUENCE: 18
ytcctcaatc cacactctrt tc                                            22

<210> SEQ ID NO 19
```

```
<211> LENGTH: 24
<212> TYPE: DNA
<213> ORGANISM: Zika virus

<400> SEQUENCE: 19
acctggtcaa tccatggaaa ggga                                              24

<210> SEQ ID NO 20
<211> LENGTH: 109
<212> TYPE: DNA
<213> ORGANISM: Zika virus

<400> SEQUENCE: 20
agttgactgg gttccaactg ggagaactac ctggtcaatc catggaaagg gagaatggat       60
gaccactgaa gacatgcttg tggtgtggaa cagagtgtgg attgaggag                  109

<210> SEQ ID NO 21
<211> LENGTH: 21
<212> TYPE: DNA
<213> ORGANISM: Zika virus

<400> SEQUENCE: 21
ccayttcaac aarctsyayc t                                                 21

<210> SEQ ID NO 22
<211> LENGTH: 19
<212> TYPE: DNA
<213> ORGANISM: Zika virus

<400> SEQUENCE: 22
tttgcwarca rgcagtctc                                                    19

<210> SEQ ID NO 23
<211> LENGTH: 22
<212> TYPE: DNA
<213> ORGANISM: Zika virus

<400> SEQUENCE: 23
tgccgccacc aagatgaact ga                                                22

<210> SEQ ID NO 24
<211> LENGTH: 135
<212> TYPE: DNA
<213> ORGANISM: Zika virus

<400> SEQUENCE: 24
ccacttcaac aagctccatc tcaaggacgg gaggtccatt gtggttccct gccgccacca       60
agatgaactg attggccggg cccgcgtctc tccaggggcg ggatggagca tccgggagac      120
tgcttgccta gcaaa                                                       135

<210> SEQ ID NO 25
<211> LENGTH: 17
<212> TYPE: DNA
<213> ORGANISM: Zika virus

<400> SEQUENCE: 25
tsyagggart gcacaat                                                      17

<210> SEQ ID NO 26
<211> LENGTH: 24
<212> TYPE: DNA
<213> ORGANISM: Zika virus
```

```
<400> SEQUENCE: 26
actaagttrc tytctggttc ytty                                          24

<210> SEQ ID NO 27
<211> LENGTH: 24
<212> TYPE: DNA
<213> ORGANISM: Zika virus

<400> SEQUENCE: 27
tggtatggaa tggagataag gccc                                          24

<210> SEQ ID NO 28
<211> LENGTH: 102
<212> TYPE: DNA
<213> ORGANISM: Zika virus

<400> SEQUENCE: 28
agggagtgca caatgccccc actgtcgttc cgggctaaag atggctgttg gtatggaatg   60
gagataaggc ccaggaaaga accagaaagc aacttagtaa gg                      102

<210> SEQ ID NO 29
<211> LENGTH: 20
<212> TYPE: DNA
<213> ORGANISM: Zika virus

<400> SEQUENCE: 29
agagaccctg ggagagaaat                                               20

<210> SEQ ID NO 30
<211> LENGTH: 19
<212> TYPE: DNA
<213> ORGANISM: Zika virus

<400> SEQUENCE: 30
ctcggtgatg cctgactttt                                               19

<210> SEQ ID NO 31
<211> LENGTH: 24
<212> TYPE: DNA
<213> ORGANISM: Zika virus

<400> SEQUENCE: 31
agatgtcggc cctggagttc tact                                          24

<210> SEQ ID NO 32
<211> LENGTH: 88
<212> TYPE: DNA
<213> ORGANISM: Zika virus

<400> SEQUENCE: 32
agagaccctg ggagagaaat ggaaggcccg cttgaaccag atgtcggccc tggagttcta   60
ctcctacaaa aagtcaggca tcaccgag                                      88

<210> SEQ ID NO 33
<211> LENGTH: 19
<212> TYPE: DNA
<213> ORGANISM: Chikungunya virus

<400> SEQUENCE: 33
tttgcaagct ccagatcca                                                19
```

```
<210> SEQ ID NO 34
<211> LENGTH: 23
<212> TYPE: DNA
<213> ORGANISM: Chikungunya virus

<400> SEQUENCE: 34
gtagctgtag tgcgtaccta ttt                                              23

<210> SEQ ID NO 35
<211> LENGTH: 20
<212> TYPE: DNA
<213> ORGANISM: Chikungunya virus

<400> SEQUENCE: 35
gagaagctca gaggacccgt                                                  20

<210> SEQ ID NO 36
<211> LENGTH: 20
<212> TYPE: DNA
<213> ORGANISM: Chikungunya virus

<400> SEQUENCE: 36
gagaagctca gaggacccgt                                                  20

<210> SEQ ID NO 37
<211> LENGTH: 21
<212> TYPE: DNA
<213> ORGANISM: Chikungunya virus

<400> SEQUENCE: 37
cgttctcgca tctagccata a                                                21

<210> SEQ ID NO 38
<211> LENGTH: 23
<212> TYPE: DNA
<213> ORGANISM: Chikungunya virus

<400> SEQUENCE: 38
tgatcccgac tcaaccatcc tgg                                              23

<210> SEQ ID NO 39
<211> LENGTH: 22
<212> TYPE: DNA
<213> ORGANISM: Chickungunya virus

<400> SEQUENCE: 39
gtacttcctg tccgacatca tc                                               22

<210> SEQ ID NO 40
<211> LENGTH: 110
<212> TYPE: DNA
<213> ORGANISM: Chikungunya virus

<400> SEQUENCE: 40
cgttctcgca tctagccata aaactaatag agcaggaaat tgatcccgac tcaaccatcc      60
tggatatagg tagtgcgcca gcaaggagga tgatgtcgga caggaagtac                110

<210> SEQ ID NO 41
<211> LENGTH: 18
<212> TYPE: DNA
<213> ORGANISM: Chikungunya virus

<400> SEQUENCE: 41
```

```
cccgactcaa ccatcctg                                                    18

<210> SEQ ID NO 42
<211> LENGTH: 18
<212> TYPE: DNA
<213> ORGANISM: Chikungunya virus

<400> SEQUENCE: 42
gcagacgcag tggtactt                                                    18

<210> SEQ ID NO 43
<211> LENGTH: 22
<212> TYPE: DNA
<213> ORGANISM: Chikungunya virus

<400> SEQUENCE: 43
ccagcaagga ggatgatgtc gg                                               22

<210> SEQ ID NO 44
<211> LENGTH: 90
<212> TYPE: DNA
<213> ORGANISM: Chjkungunya virus

<400> SEQUENCE: 44
ccccgactca accatcctgg atatcggcag tgcgccagca aggaggatga tgtcggacag       60
gaagtaccag gaagtaccac tgcgtctgcc                                       90

<210> SEQ ID NO 45
<211> LENGTH: 19
<212> TYPE: DNA
<213> ORGANISM: Dengue virus

<400> SEQUENCE: 45
aaccwacgra araagrcgv                                                   19

<210> SEQ ID NO 46
<211> LENGTH: 20
<212> TYPE: DNA
<213> ORGANISM: Dengue virus

<400> SEQUENCE: 46
grgaawctct tygyyarctg                                                  20

<210> SEQ ID NO 47
<211> LENGTH: 17
<212> TYPE: DNA
<213> ORGANISM: Dengue virus

<400> SEQUENCE: 47
tcaatatgct gaaacgc                                                     17

<210> SEQ ID NO 48
<211> LENGTH: 95
<212> TYPE: DNA
<213> ORGANISM: Dengue virus

<400> SEQUENCE: 48
aacctacgaa aaaagacggc tcgaccgtct ttcaatatgc tgaaacgcgc gagaaaccgc       60
gtgtcaactg tttcacagtt ggcgaagaga ttctc                                 95

<210> SEQ ID NO 49
```

```
<211> LENGTH: 28
<212> TYPE: DNA
<213> ORGANISM: Babesia microti

<400> SEQUENCE: 49
cctaggtatg tatcatctta acctcttt                                          28

<210> SEQ ID NO 50
<211> LENGTH: 22
<212> TYPE: DNA
<213> ORGANISM: Babesia microti

<400> SEQUENCE: 50
tagggatcgt agtcgtgtac tg                                                22

<210> SEQ ID NO 51
<211> LENGTH: 30
<212> TYPE: DNA
<213> ORGANISM: Babesia microti

<400> SEQUENCE: 51
cccaagtagg tatctatgta cttctactgt                                        30

<210> SEQ ID NO 52
<211> LENGTH: 125
<212> TYPE: DNA
<213> ORGANISM: Babesia microti

<400> SEQUENCE: 52
gttacctagg tatgtatcat cttaacctct ttactaccca agtaggtatc tatgtacttc       60
tactgtacct actaatagga caaacaagtg taacttgtag cagtacacga ctacgatccc      120
tatag                                                                  125

<210> SEQ ID NO 53
<211> LENGTH: 20
<212> TYPE: DNA
<213> ORGANISM: Lassa virus

<400> SEQUENCE: 53
tctctgacat ctgtctcgca                                                   20

<210> SEQ ID NO 54
<211> LENGTH: 21
<212> TYPE: DNA
<213> ORGANISM: Lassa virus

<400> SEQUENCE: 54
gttgcagcag ctcttcacaa t                                                 21

<210> SEQ ID NO 55
<211> LENGTH: 287
<212> TYPE: DNA
<213> ORGANISM: Lassa virus

<400> SEQUENCE: 55
cgaagtgcgt ctagtccttg tatccaaggc aaatctaccc agtctctgac atctgtctcg       60
caattcaata agaatgggtc aatagggtat cttgcatatt gcaaaagact taaggttctt      120
ttctgtatta gattgcacag gtgaacaggg acaccattcg caaccgactg atcaatgatt      180
gtgtcaattg tttctgccag ttggtgtggc tctttacact ttatattgtg aagagctgct      240
gcaacgaact tgtctaagc aagagtctgc gactcctgtg gatctac                     287
```

-continued

```
<210> SEQ ID NO 56
<211> LENGTH: 21
<212> TYPE: DNA
<213> ORGANISM: Lassa virus

<400> SEQUENCE: 56
yacagggtcy tctggwcgac c                                              21

<210> SEQ ID NO 57
<211> LENGTH: 21
<212> TYPE: DNA
<213> ORGANISM: Lassa virus

<400> SEQUENCE: 57
ratgatgcar cttgacccaa g                                              21

<210> SEQ ID NO 58
<211> LENGTH: 127
<212> TYPE: DNA
<213> ORGANISM: Lassa virus

<400> SEQUENCE: 58
gcccgacata ggttggtaaa gagctatttc cacagggtct tctggacgac cttcaatgtc    60
tatccaggtt ttggcacttg ggtcaagctg catcattgag tctttaagtg tcatcaactg   120
agaatag                                                             127
```

NUCLEIC ACID AMPLIFICATION ASSAYS FOR DETECTION OF PATHOGENS

CROSS REFERENCE TO RELATED APPLICATIONS

This application is a U.S. National Stage of International Application No. PCT/US2017/048744, filed Aug. 25, 2017, which claims the benefit of U.S. Provisional Application No. 62/380,353 filed Aug. 26, 2016. The entire contents of the above-identified priority applications are hereby fully incorporated herein by reference.

STATEMENT REGARDING FEDERALLY SPONSORED RESEARCH

This invention was made with government support under Grant No. AI10818 awarded by the National Institutes of Health, and Grant No. D18AC00006 awarded by the Department of Defense. The government has certain rights in the invention.

FIELD OF THE INVENTION

The present invention provides a combination of genomic and computational technologies to provide rapid, portable sample analysis for identifying a target sequence.

BACKGROUND OF THE INVENTION

Infectious diseases cause tremendous morbidity and mortality in tropical developing countries, and the need for a holistic approach to their detection and diagnosis is increasingly clear. The full range and prevalence of pathogens in such settings is not well understood, and the capacity to detect new or infrequent threats, like Ebola, is often lacking. The ability to diagnose a broad spectrum of pathogens is vital, since infection with multiple pathogens and resulting misdiagnoses are common.

First, there is a need in patient care for more comprehensive diagnostic tests. Many pathogens produce non-specific symptoms like fever, headache, and nausea, making them difficult to distinguish clinically. For example, 30%-90% of hospitalized patients with acute fever in tropical Africa are diagnosed with malaria and treated accordingly, while only 7%-45% of them actually have laboratory-confirmed malaria. Better tests for individual diseases will be useful, but will not fully solve the problem: e.g., many patients with detectable malaria are actually sick because of other infections. Such misdiagnoses can be fatal, as in a 1989 outbreak of Lassa fever in two Nigerian hospitals, where 22 people died. Thus, Applicants have developed a low-cost PCR-based panel for a range of infectious diseases as a routine diagnostic procedure for febrile patients.

Second, there is a need to better understand the array of existing pathogens and to detect emerging threats. Lassa virus, once thought to be a novel cause of sporadic disease outbreaks, has turned out to be endemic in much of West Africa, and there is even evidence that Ebola circulates undetected more widely than is supposed. Any samples that fail Applicants' diagnostic panel, therefore, are sent for deep metagenomic sequencing to detect other pathogens. A random selection of other samples is treated the same way, to provide a broad picture of the range of pathogens in the region, which in turn will enable early detection of new or increasing pathogens.

Technological advances in sequencing and analyzing the genomes of a wide variety of microbes, including the costs of implementing genomic approaches at scale, make it possible to address these needs. However, to fulfill that promise, the tools must be delivered to researchers and clinicians on the ground. Empowering local health care clinics and their communities, in turn, will help motivate patients to seek care at the clinic. In addition to saving lives, this enables us to continually monitor patients with unexplained fever, capturing diseases that previously went undiagnosed or misdiagnosed. After local diagnosis, samples can then be sent to advanced laboratories in the US—and hopefully soon Africa too—for in-depth analysis using high-throughput metagenomic sequencing. Discoveries of new pathogens can then be converted into affordable, field-deployable diagnostics to inform health care workers and the populations they serve, reducing the burden of disease, and improving local capacity to detect and treat at the earliest possible stages. Robust data systems are needed to connect sample collections, the process of pathogen identification, and candidates for developing diagnostics and treatments. By comprehensively identifying pathogens circulating in the population this new infrastructure serves as an early warning for emerging and persistent diseases. With their own diagnostic capacity for a wide range of infectious agents, sites throughout Africa are able to support their communities and help to detect, monitor and characterize emerging diseases before they become global threats.

SUMMARY OF THE INVENTION

Embodiments disclosed herein are directed to methods of identifying highly conserved regions among pathogen variants and/or pathogen species and use of primers and probes directed to such regions for the development and use of nucleic acid-based detection assays for detection of pathogens.

In one aspect, the invention provides a method for developing probes and primers to pathogens, comprising: providing a set of input genomic sequences to one or more target pathogens; generating a set of target sequences from the set of input genomic sequences; applying a set cover solving process to the set of target sequences to identify one or more target amplification sequences, wherein the one or more target amplification sequences are highly conserved target sequences shared between the set of input genomic sequences of the target pathogen; and generating one or more primers, one or more probes, or a primer pair and probe combination based on the one or more target amplification sequences. In one embodiment, the set of input genomic sequences represent genomic sequences from two or more variants of the target pathogen. In another embodiment, the set input genomic sequences represent genomic sequence from two or more target pathogens. In another embodiment, the one or more target pathogens is one or more viral pathogens. In another embodiment, the viral pathogen is Zika, Chikungunya, Ebola Dengue, Lassa, or a combination thereof. In another embodiment, the one or more pathogens is a parasitic pathogen. In another embodiment, the parasitic pathogen is *Babesia microti*. In another embodiment, the target sequences are fragmented to a size that is approximately equal to a size of an amplicon for detection using a nucleic acid amplification assay. In another embodiment, the size of the target sequence is 100 to 500 base pairs. In another embodiment, each nucleotide of the set of input genomic sequences is considered an element of universe of the set cover solving process and wherein each element is considered covered if the target sequence aligns to some portion of a genomic reference sequence.

In another aspect, the invention provides a method for detecting one or more pathogens comprising: contacting a sample with one or more primers and/or probes generated using a method as described herein; and detecting amplification of one or more pathogen target sequences using a nucleic acid amplification method and the one or more primers and/or probes, wherein detection of the target sequence indicates a presence of the one or more pathogens in the sample. In one embodiment, the nucleic acid amplification method is quantitative PCR and the one or more primers and/or probes comprise a forward and reverse primers and a probe modified with a detectable label. In another embodiment, the forward primer comprises one or more of SEQ ID NOs: 1, 5, 9, 13, 17, 21, 25, 29, 33, 37, 41, 45, 49, 53, and 56, the reverse primer comprises one or more of SEQ ID NOs: 2, 6, 10, 14, 18, 22, 26, 30, 34, 48, 42, 46, 50, 54, and 57, and the probe comprises one or more of SEQ ID NOs: 3, 7, 11, 15, 19, 23, 27, 31, 35, 39, 43, 47, and 51.

In another aspect, the invention provides a method for detecting Zika and/or Chikungunya in samples, comprising: contacting a sample with a forward and reverse primer and a probe with a detectable label, wherein the forward primer comprises one or more of SEQ ID NOs: 5, 9, 13, 17, 21, 25, 29, 33, 37, or 41, the reverse primer comprises one or more of SEQ ID NOs: 6, 10, 14, 18, 22, 26, 30, 34, 38, and 43, and the probe comprises one or more of SEQ ID NOs: 7, 11, 15, 19, 23, 27, 31, 35, 39, and 43; and detecting amplification of one or more target sequences through a quantitative PCR assay using the forward and reverse primers and the probe, wherein detection of the one or more target sequences indicates the presence of Zika, Chikungunya, or both. In another example embodiment for detecting Zika and/or Chikungunya in samples comprises; contacting a sample with a forward primer, a reverse primer, and a probe with a detectable label and configured to hybridize to at least one of the target sequences of SEQ ID Nos: 4, 8, 12, 16, 20, 24, 28, 32, 36, 40, or 44; and detecting amplification of the one or more target sequences by quantitative PCR using the forward primer, the reverse, primer, the probe, wherein detection of the one or more target sequences indicates the presence of Zika, Chikungunya, or both in the samples.

In another aspect, the invention provides a method for detecting Ebola in samples, comprising: contacting a sample with a forward and reverse primer and a probe with a detectable label, wherein the forward primer comprises SEQ ID NO: 1, the reverse primer comprises SEQ ID NO: 2, and the probe comprises SEQ ID NO:3; and detecting amplification of one or more target sequences by quantitative PCR using the forward primer, reverse primer, and the probe, wherein detection of the one or more target sequences indicates the presence of Ebola. In another example embodiment, detecting Ebola in samples comprises; contacting a sample with a forward primer, a reverse primer, and a probe with a detectable label and each configured to hybridize to at least a portion of SEQ ID NO: 4; and detecting amplification of the target sequence by quantitative PCR using the forward primer, the reverse primer, and the probe, wherein detection of the target sequence indicates the presence of Ebola in the sample.

In another aspect, the invention provides a method for detecting Dengue in samples, comprising: contacting a sample with a forward primer, a reverse primer and a probe with a detectable label, wherein the forward primer comprises SEQ ID NO: 45, the reverse primer comprises SEQ ID NO: 46, and the probe comprises SEQ ID NO: 47; and detecting amplification of one or more target sequences by quantitative PCR using the forward primer, reverse primer, and the probe, wherein detection of the one or more target sequences indicates the presence of Dengue. In another example embodiment, a method for Dengue in samples comprise; contacting a sample with a forward and reverse primer and a probe with a detectable label each configured to hybridize to a portion of target sequence of SEQ ID NO: 48; and detecting amplification of the target sequence by quantitative PCR using the forward primer, the reverse primer, and the probe, wherein detection of the target sequence indicates the presence of Dengue in the sample.

In another aspect, the invention provides a method for detecting Lassa in samples, comprising: contacting a sample with a forward primer, and reverse primer wherein the forward primer comprises SEQ ID NOs: 53 or 56, the reverse primer comprises SEQ ID NOs: 54 or 57, and detecting amplification of one or more target sequences by quantitative PCR using the forward primer, reverse primer, and the probe, wherein detection of the one or more target sequences indicates the presence of Lassa. In another example embodiment, a method for detecting Lassa in samples comprises contacting a sample with a forward and reverser primer each configured to hybridize to at least a portion of the target sequence of SEQ ID NO: 55, SEQ ID NO: 58, or both; and detecting amplification of the one or both of the target sequences using the forward primer and reverse primer, wherein detection of one or both of the target sequences indicates the presence of Lassa in the sample.

In another aspect, the invention provides a method for detecting *Babesia microti* in samples, comprising: contacting a sample with a forward and reverse primer and a probe with a detectable label, each configured to hybridize to at least a portion of SEQ ID NO: 52; and detecting amplification of the target sequence by quantitative PCR using the forward primer, the reverse primer, and the probe, wherein detection of the one or more target sequences indicates the presence of *B. microti* in the sample. In another example embodiment, a method for detecting *B. microti* in samples, comprises: contacting a sample with a forward and reverse primer and a probe with a detectable lable, wherein the forward primer comprises SEQ ID NO: 49, the reverse primer comprises SEQ ID NO: 50, and the probe comprises SEQ ID NO: 54; and detecting amplification of one or more target sequences by quantitative PCR using the forward primer, reverse primer, and the probe, wherein detection of the one or more target sequences indicates the presence of *B. microti*.

In another aspect, the invention provides a kit comprising the primers and/or probes of a method as described herein.

These and other aspects, objects, features, and advantages of the example embodiments will become apparent to those having ordinary skill in the art upon consideration of the following detailed description of the illustrated embodiments.

BRIEF DESCRIPTION OF THE DRAWINGS

FIG. 3—Shows an overview of the diagnostics of Zika virus.

FIG. 6—Shows Zika RT-qPCR assays and nucleotide mismatches across Zika strains.

FIG. 11—Shows results from newly designed assays against NS1NS3, NS5 regions of Zika virus.

FIG. 13—Shows results of Zika NS5 probe-based diagnostic assay.

FIG. 15—Shows primers and probes for detection of Zika virus.

DETAILED DESCRIPTION OF THE INVENTION

General Definitions

Figure 1:
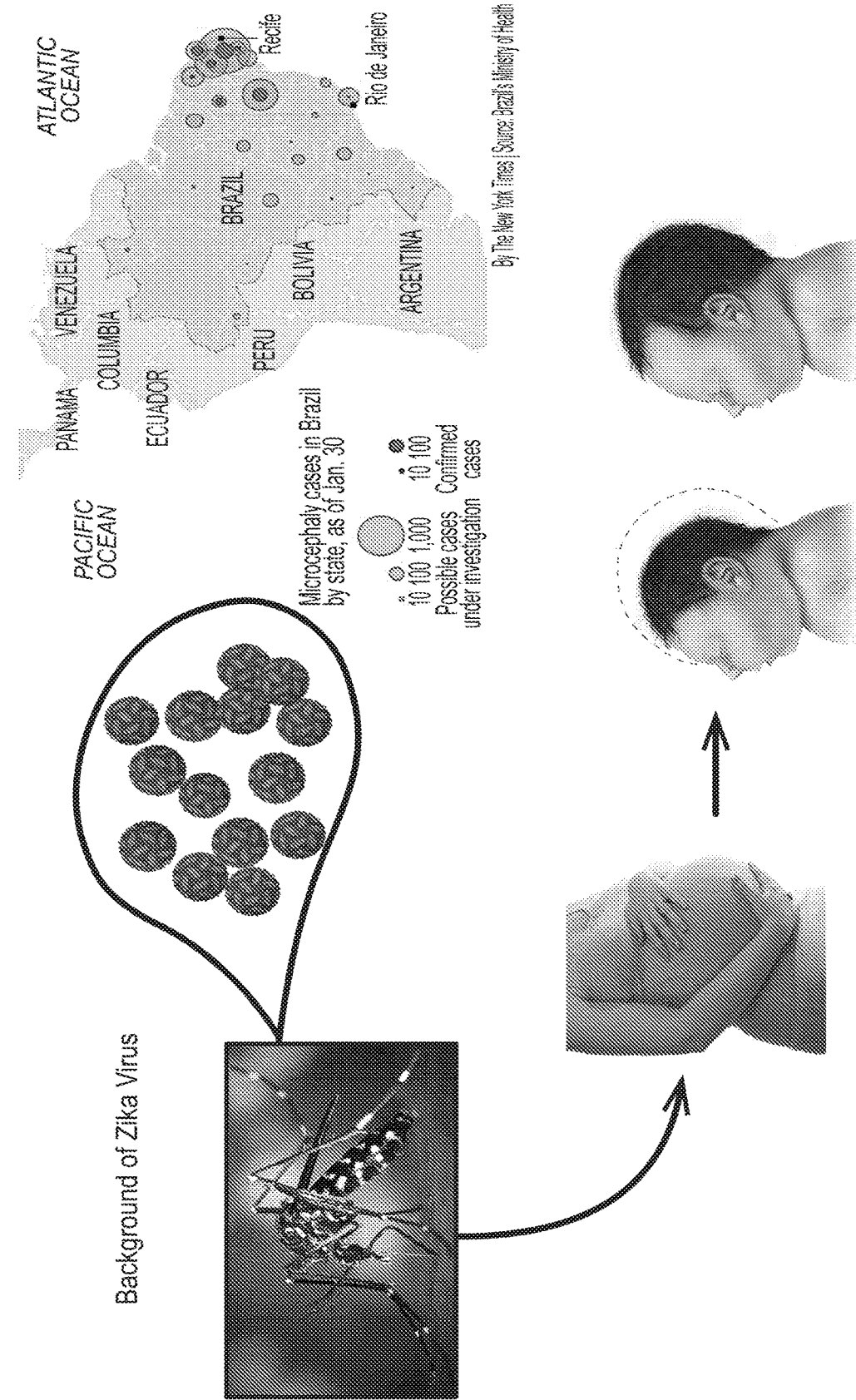
FIG. 1—Shows the background of Zika virus.

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual. 2nd edition (1989) (Sambrook, Fritsch, and Maniatis); Molecular Cloning: A Laboratory Manual, 4th edition (2012) (Green and Sambrook); Current Protocols in Molecular Biology (1937) (F. M. Ausubel et. al. eds.); the series Methods in Enzymology (Academic Press, Inc.): PCR 2: A Practical Approach (1995) (M. J MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R. I. Fresliney, ed.); Benjamin Lewin, Genes IX, published by Jones and Bartlett, 2008 (ISBN 0763752223); Kendrew et a. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780171185710); Singleton et al., Dictionary of Microbiology and Molecular Biology 2nd ed., I Wiley & Sons (New York, N Y, 1994). March, Advanced Organic Chemistry Reactions, Mechanisms and Structure 4th ed., John Wiley & Sons (New York, NY. 1992); and Marten H, Hofker and Jan van Deursen, Transgenic Mouse Methods and Protocol, 2nd edition (2011).

As used herein, the singular forms "a", "an", and "the" include both singular and plural referents unless the context clearly dictates otherwise.

As used herein the term "hybridize" or "hybridization refers to ability of oligonucleotides and their analogs to hybridize by hydrogen bonding, which includes Watson-Crick, Hoogsteen, or reversed Hoogsteen hydrogen bonding, between complementary bases, Generally nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C "Complementary" refers to the base pairing that occurs between two distinct nucleic acid sequences or two distinct regions of the same nucleic acid sequence.

Specifically hybridizable" and "specifically complementary" are terms that indicate a sufficient degree of complementarity such that stable and specific binding occurs between the oligonucleotide (or it's analog) and the DNA or RNA target. The oligonucleotide or oligonucleotide analog need not be 100% complementary to its target sequence to be specifically hybridizable. An oligonucleotide or analog is specifically hybridizable when there is a sufficient degree of complementarity to avoid non-specific binding of the oligonucleotide or analog to non-target sequences under conditions where specific binding is desired. Such binding is referred to as specific hybridization.

The identity/similarity between two or more nucleic acid sequences, or two or more amino acid sequences, is expressed in terms of the identity or similarity between the sequences. Sequence identity can be measured in terms of percentage identity: the higher the percentage, the more identical the sequences are. Homologs or orthologs of nucleic acid or amino acid sequences possess a relatively high degree of sequence identity/similarity when aligned using standard methods, Methods of alignment of sequences for comparison are well known in the art. Various programs and alignment algorithms are described in: Smith & Waterman, Adv. Appl. Math. 2482 1981; Needleman & Wunsch. J. Mol. Biol. 48:443, 1970; Pearson & Lipman, Proc. Natl. Acad. Sci. USA 85:2444, 1988; Higgins & Sharp, Gene, 73:237-44, 1988, Higgins & Sharp, CABIOS 5:151-3, 1989: Corpet et al., Nuc. Acids Res. 16:10881-90, 1988; Huang et al. Computer Appls, in the Biosciences 8, 155-65, 1992, and Pearson et al., Meth. Mol. Bio. 24:307-31, 1994. Altschul et al., J. Mol. Biol. 215:403-10, 1990, presents a detailed consideration of sequence alignment methods and homology calculations. The NCBI Basic Local Alignment Search Tool (BLAST) (Altschul et al., J. Mol. Biol. 215:403-10, 1990) is available from several sources, including the National Center for Biological Information (NCBI, National Library of Medicine, Building 38A, Room 8N805, Bethesda, MD 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded tip to 75.2. The length value will always be an integer. In another example, a target sequence containing a 20-nucleotide region that aligns with 20 consecutive nucleotides from an identified sequence as follows contains a region that shares 75 percent sequence identity to that identified sequence (i.e., 15÷20*100=75).

The term "amplification" refers to methods to increase the number of copies of a nucleic acid molecule. The resulting amplification products are typically called "amplicons." Amplification of a nucleic acid molecule (such as a DNA or RNA molecule) refers to use of a technique that increases the number of copies of a nucleic acid molecule (including fragments). In some examples, an amplicon is a nucleic acid from a cell, or acellular system, such as mRNA or DNA that has been amplified.

An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative real-time PCR; reverse transcriptase PCR (RT-PCR); real-time PCR (rt PCR); real-time reverse transcriptase PCR (rt RT-PCR); nested PCR; strand displacement amplification (see U.S. Pat. No. 5,744,311); transcription-free isothermal amplification (see U.S. Pat. No. 6,033,881, repair chain reaction amplification (see WO 90/01069): ligase chain reaction amplification (see European patent publication EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134) amongst others.

The term "primer" or "primers" refers to short nucleic acid molecules, such as a DNA oligonucleotide, for example sequences of at least 15 nucleotides, which can be annealed to a complementary nucleic acid molecule by nucleic acid hybridization to form a hybrid between the primer and the nucleic acid strand. A primer can be extended along the nucleic acid molecule by a polymerase enzyme. Therefore, primers can be used to amplify a nucleic acid molecule, wherein the sequence of the primer is specific for the nucleic acid molecule, for example so that the primer will hybridize to the nucleic acid molecule under very high stringency hybridization conditions. The specificity of a primer increases with its length. Thus, for example, a primer that includes 30 consecutive nucleotides will anneal to a sequence with a higher specificity than a corresponding primer of only 15 nucleotides. Thus, to obtain greater specificity, probes and primers can be selected that include at least 15, 20, 25, 30, 35, 40, 45, 50 or more consecutive nucleotides.

In particular examples, a primer is at least 15 nucleotides in length, such as at least 15 contiguous nucleotides complementary to a nucleic acid molecule. Particular lengths of primers that can be used to practice the methods of the present disclosure, include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, or more contiguous nucleotides complementary to the target nucleic acid molecule to be amplified, such as a primer of 15-60 nucleotides, 15-50(nucleotides, or 15-30 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence, In general, at least one forward and one reverse primer are included in an amplification reaction. PCR primer pairs can be derived from a known sequence, for example, by using computer programs intended for that purpose such as Primer (Version 0.5, © 1991, Whitehead Institute for Biomedical Research, Cambridge, MA).

The term "probe" refers to an isolated nucleic acid capable of hybridizing to a specific nucleic acid (such as a nucleic acid barcode or target nucleic acid) A detectable label or reporter molecule can be attached to a probe. Typical labels include radioactive isotopes, enzyme substrates, co-factors, ligands, chemiluminescent or fluorescent agents, haptens, and enzymes. In some example, a probe is used to isolate and/or detect a specific nucleic acid.

Methods for labeling and guidance in the choice of labels appropriate for various purposes are discussed, for example, in Sambrook et al., Molecular Cloning: A Laboratory Manual, Cold Spring Harbor Laboratory Press (1989) and Ausubel et al., Current Protocols in Molecular Biology, Greene Publishing Associates and Wiley-Intersciences (1987).

Probes are generally about 15 nucleotides in length to about 160 nucleotides in length, such as 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 15, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 38, 89, 90, 91, 92, 93, 94, 95, 96, 97, 98, 99, 100, 101, 102, 103, 104, 105, 106, 107, 108, 109, 140, 11, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 contiguous nucleotides complementary to the specific nucleic acid molecule, such as 50-140 nucleotides, 75-150 nucleotides, 60-70 nucleotides, 30-130 nucleotides, 20-60 nucleotides, 20-50 nucleotides, 20-40 nucleotides, or 20-30 nucleotides.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/1% or less, and +/−0.1% or less of and from the specified value, insofar such variations are appropriate to perform in the disclosed invention. It is to be understood that the value to which the modifier"about" or"approximately" refers is itself also specifically, and preferably, disclosed.

Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication published patent document, or patent application was specifically and individually indicated as being incorporated by reference.

Overview

Future pandemics threaten human progress and must be detected early. The goal of the present study was to achieve a sustainable, rapid-response surveillance system to detect infectious disease outbreaks as soon as they appear. To do so, vast improvement is needed in both diagnostic tools and the human resources to deploy them. The present invention therefore relates to developing rapid pathogen sequencing for comprehensive microbial detection.

Rapid advances in DNA amplification and detection technology provide an unprecedented capability to identify and characterize pathogens, and will soon enable comprehensive and unbiased pathogen surveillance for early detection and prevention of future epidemics. However, realizing its full potential for infectious disease surveillance and clinical diagnosis present additional challenges, which require further investment and focused effort.

The present invention relates to a method for generating primers and/or probes for use in analyzing a sample which may comprise a pathogen target sequence comprising providing a set of input genomic sequence to one or more target pathogens, generating a set of target sequences from the set of input genomic sequences, identifying one or more highly conserved target sequences, and generating one or more primers, one or more probes, or a primer pair and probe combination based on the one or more conserved target sequences.

In certain example embodiments, the methods for identifying highly conserved sequences between genomic sequences of one or more target pathogens may comprise use a set cover solving process. The set cover solving process may identify the minimal number of probes needed to cover an one or more conserved target sequence. Set cover approaches have been used previously to identify primers and/or microarray probes, typically in the 20 to 50 base pair range. See, e.g. Pearson et al., cs.virginia.edu/~robins/papers/primers_dam11_final.pdf, Jabado et al. *Nucleic Acids Res.* 2006 34(22):6605-11, Jabado et al. *Nucleic Acids Res.* 2008, 36(1):e3 doi10.1093/nar/gkm1106, Duitama et al. *Nucleic Acids Res.* 2009, 37(8):2483-2492, Phillippy et al. *BMC Bioinformatics.* 2009, 10:293 doi:10.1186/1471-2105-10-293. However, such approaches generally involved treating each primer/probe as k-mers and searching for exact matches or allowing for inexact matches using suffix arrays.

In addition, the methods generally take a binary approach to detecting hybridization by selecting primers or probes such that each input sequence only needs to be bound by one primer or probe and the position of this binding along the sequence is irrelevant. Alternative methods may divide a target genome into pre-defined windows and effectively treat each window as a separate input sequence under the binary approach—i.e., they determine whether a given primer or probe binds within each window and require that all of the windows be bound by the state of some primer or probe. Effectively, these approaches treat each element of the "universe" in the set cover problem as being either an entire input sequence or a pre-defined window of an input sequence, and each element is considered "covered" if the start of a probe binds within the element. These approaches limit the fluidity to which different primer or probe designs are allowed to cover a given target sequence.

In contrast, the methods disclosed herein take a pan-target sequence approach capable of defining a probe set that can identify and increase the sensitivity of pathogen detection assays by identifying highly conserved regions shared among multiple variants of the same pathogen or across different pathogens. For example, the methods disclosed herein may be used to identify all variants of a given virus, or multiple different viruses in a single assay. In addition, the methods disclosed herein may be used to detect all variants of a parasitic pathogen, or multiple different parasitic pathogens in a single assay. Further, the methods disclosed herein treat each element of the "universe" in the set cover problem as being a nucleotide of a target sequence, and each element is considered "covered" as long as a probe binds to some segment of a target genome that includes the element. Instead of the binary approach of previous methods, the methods disclosed herein better model how a probe, and in particular larger probes, may hybridize to a target sequence. Rather than only asking if a given sequence does or does not bind to a given window, embodiments disclosed herein first determine a hybridization pattern—i.e., where a given probe binds to a target sequence or target sequences—and then determines from those hybridization patterns of highly conserved sequences with low to no variability between sequences. These hybridization patterns may be determined by defining certain parameters that minimize a loss function, thereby enabling identification of minimal primer and probe sets in a way that allows parameters to vary for each species, e.g., to reflect the diversity of each species, as well as in a computationally efficient manner that cannot be achieved using a straightforward application of a set cover solution, such as those previously applied in the primer and microarray probe design context.

A primer in accordance with the invention may be an oligonucleotide for example deoxyribonucleic acid (DNA), ribonucleic acid (RNA), peptide nucleic acid (PNA), or other non-naturally occurring nucleic acid. A probe, a candidate probe, or a selected probe may be a nucleic acid sequence, the nucleic acid being, for example, deoxyribonucleic acid (DNA), ribonucleic acid (RNA), peptide nucleic acid (PNA), or other non-naturally occurring nucleic acid.

A sample as described herein may be a biological sample, for example a blood, buccal, cell, cerebrospinal fluid, mucus, saliva, semen, tissue, tumor, feces, urine, and/or vaginal sample. A sample may be obtained from an animal, a plant, or a fungus. The animal may be a mammal. The mammal may be a primate. The primate may be a human. In other embodiments, the sample may be an environmental sample, such as water, soil, or a surface, such as an industrial or medical surface.

As used herein, "target sequence" is intended to designate either one target sequence or more than one target sequence, i.e., any sequence of interest at which the analysis is aimed. Thus, the sample may comprise more than one target sequence and preferably a plurality of target sequences. The target sequence may be a nucleotide sequence. The nucleotide sequence may be a DNA sequence, a RNA sequence, or a mixture thereof.

The set of target sequences may comprise obtaining a nucleic acid array (e.g., a microarray chip) and synthesizing a set of synthetic oligonucleotides, and removing the oligonucleotides from the microarray (e.g., by cleavage or elution) to produce a set of target sequences. Synthesis of oligonucleotides in an array format (e.g., chip) permits synthesis of a large number of sequences simultaneously, thereby providing a set of target sequences for the methods of selection. The array synthesis also has the advantages of being customizable and capable of producing long oligonucleotides.

The target sequences may be prepared from the whole genome of the target pathogen, for example, where the target sequences are prepared by a method that includes fragmenting genomic DNA of the target pathogen (e.g., where the fragmented target sequences are end-labeled with oligonucleotide sequences suitable for PCR amplification or where the target sequences are prepared by a method including attaching an RNA promoter sequence to the genomic DNA fragments and preparing the target sequences by transcribing (e.g., using biotinylated ribonucleotides) the DNA fragments into RNA. The target sequences may be prepared from specific regions of the target organism genome (e.g., are prepared synthetically). In certain embodiments, the target sequences are labeled with an affinity tag. In certain example embodiments, the affinity tag is biotin, a hapten, or an affinity tag, or the target sequences are generated using biotinylated primers, e.g., where the target sequences are generated by nick-translation labeling of purified target organism DNA with biotinylated deoxynucleotides. In cases where the target sequences are biotinylated, the target DNA can be captured using a streptavidin molecule attached to a solid phase. The target sequences may be appended by adapter sequences suitable for PCR amplification, sequencing, or RNA transcription. The target sequences may include a RNA promoter or are RNA molecules prepared from DNA containing an RNA promoter (e.g., a T7 RNA promoter).

Figure 2:
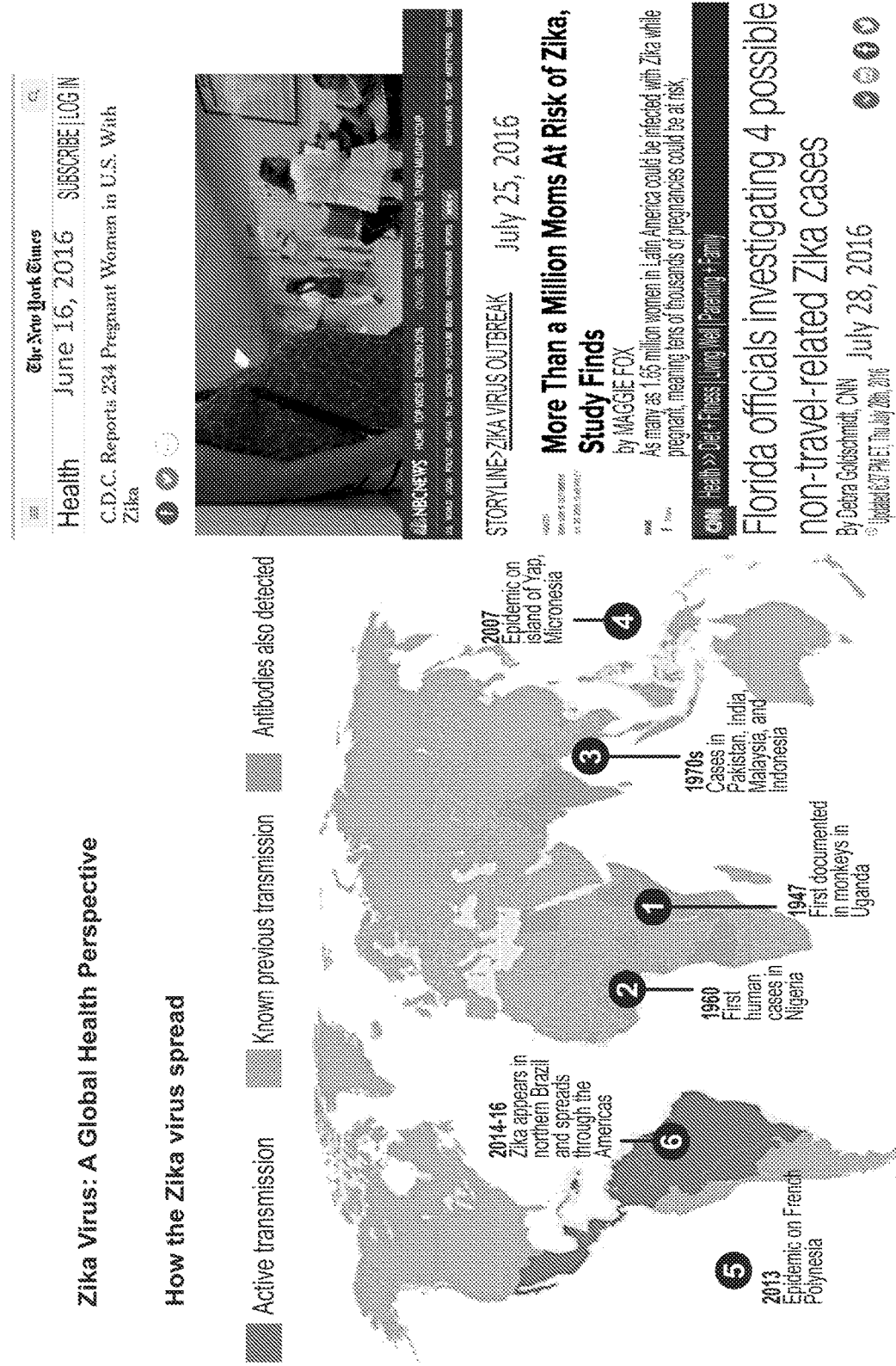
FIG. 2—Shows the global health perspective of Zika virus.
Figure 4:
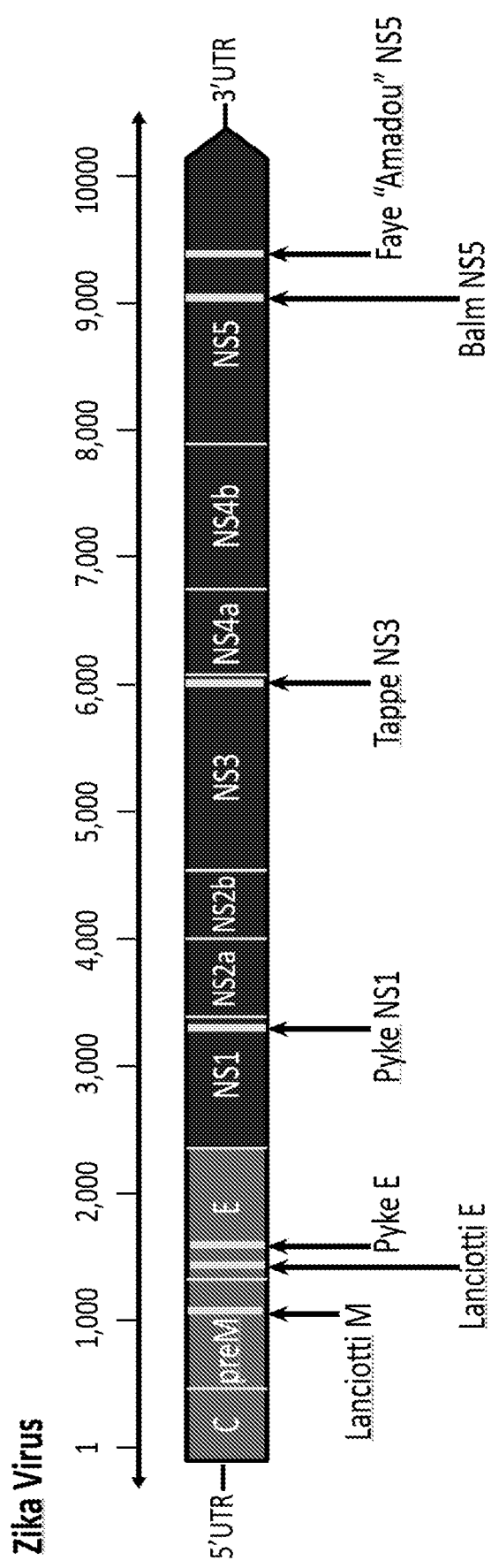
FIG. 4—Shows a diagram of the Zika virus genome.
Figure 5:
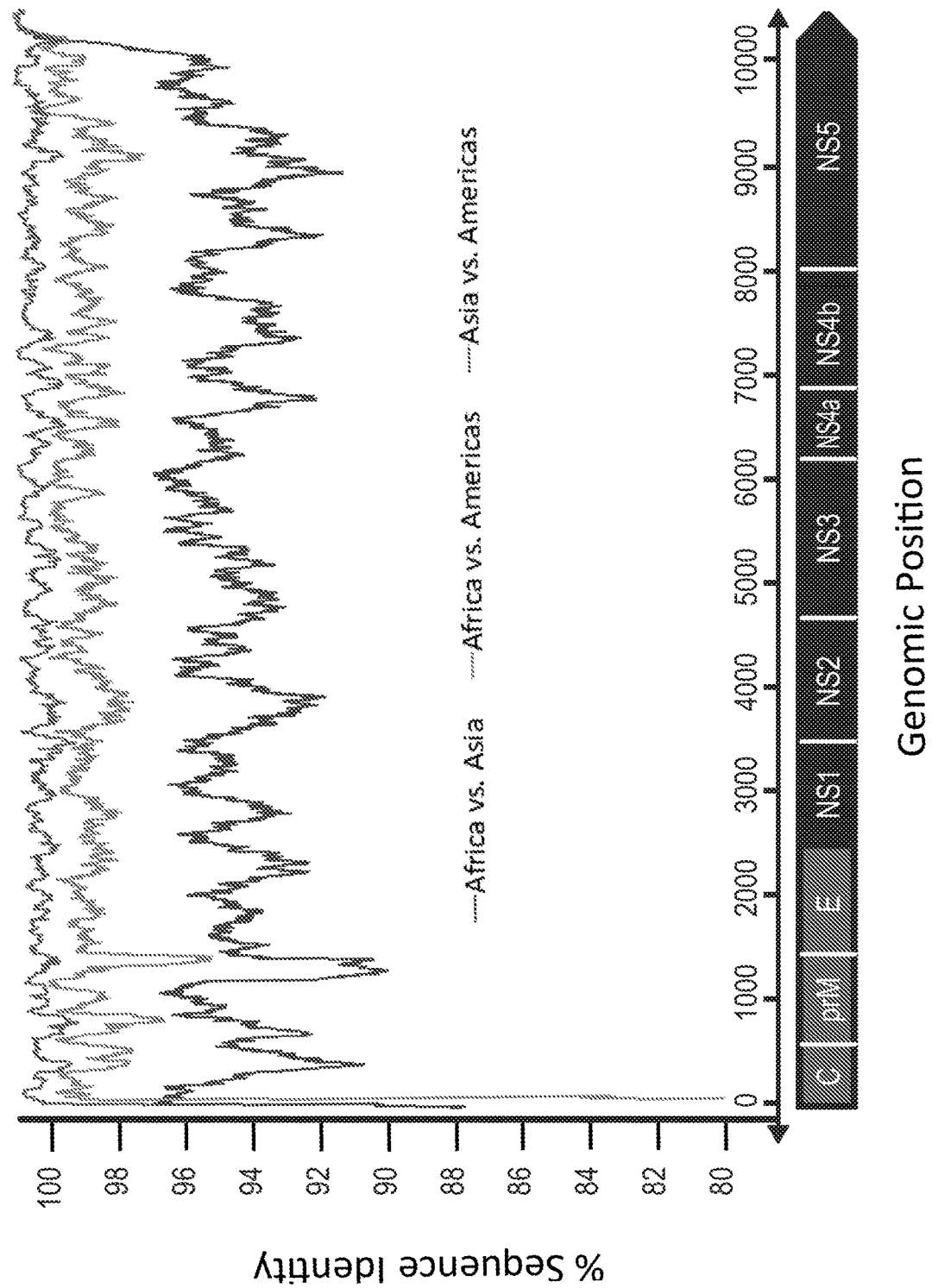
FIG. 5—Shows a plot of the percent genomic identity of all global Zika virus strains.
Figure 7:
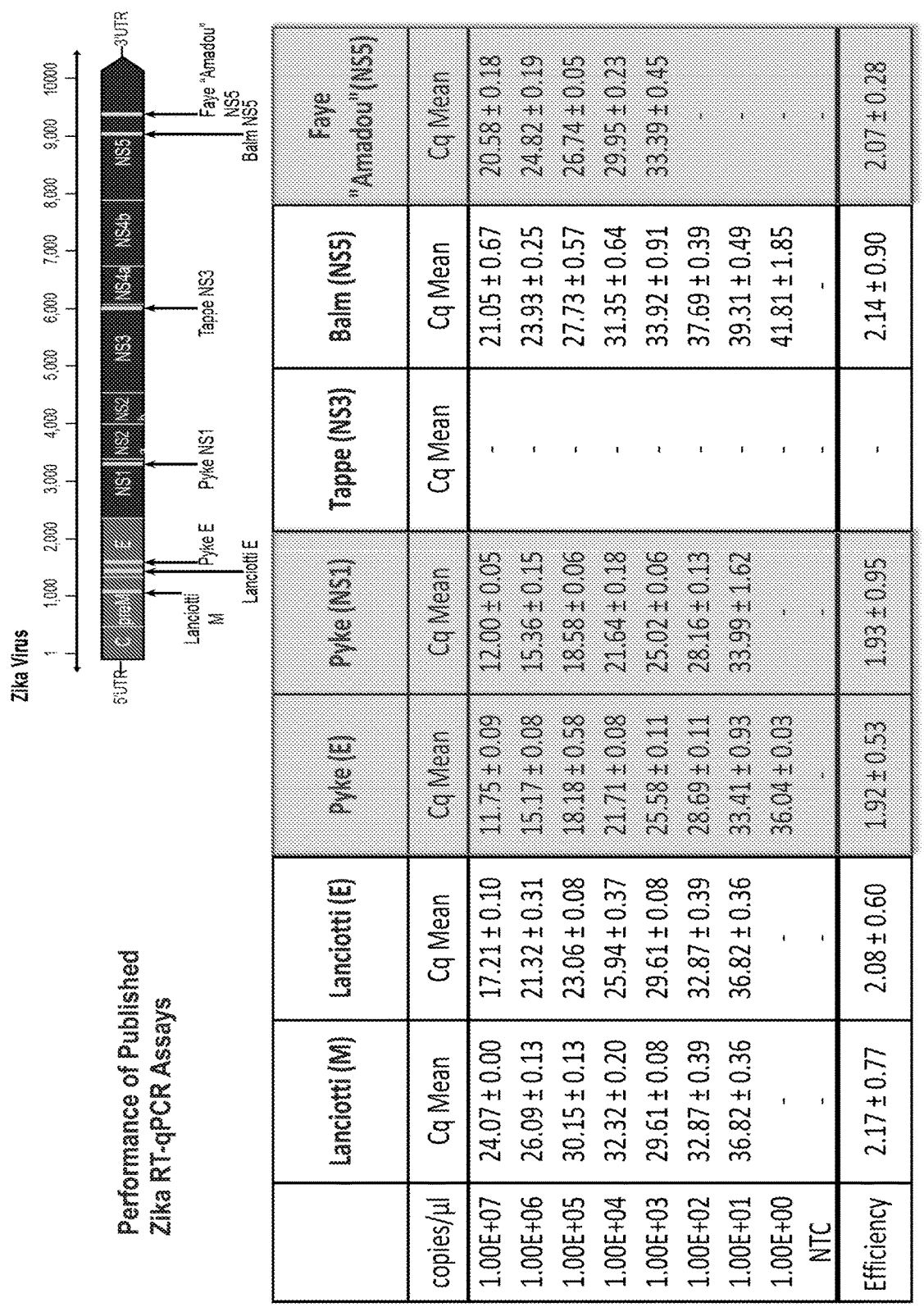
FIG. 7—Shows performance data for Zika RT-qPCR assays.
Figure 8:
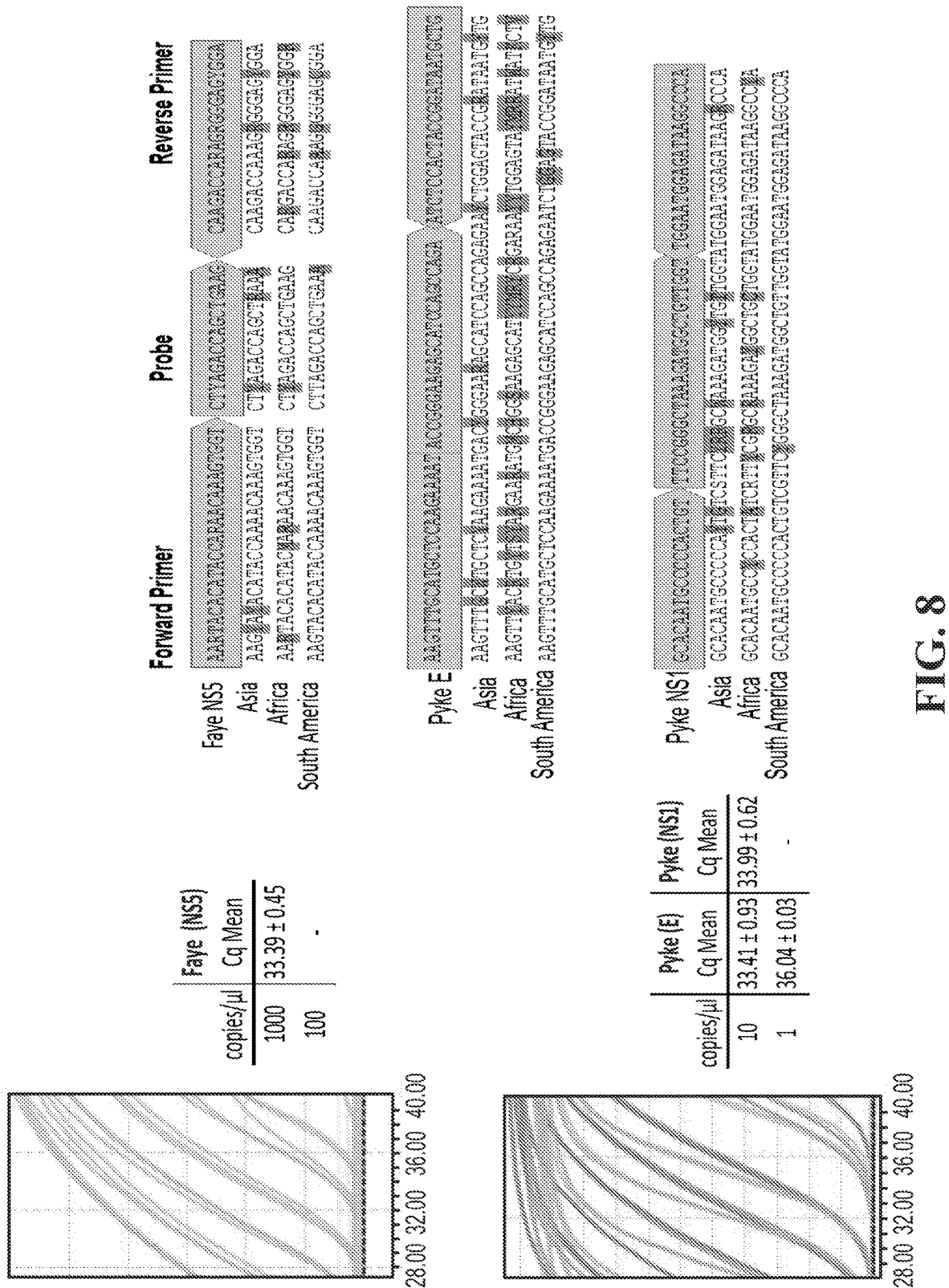
FIG. 8—Shows standard curves for three Zika assays, FAYE, Pyke E, and NS1.
Figure 9:
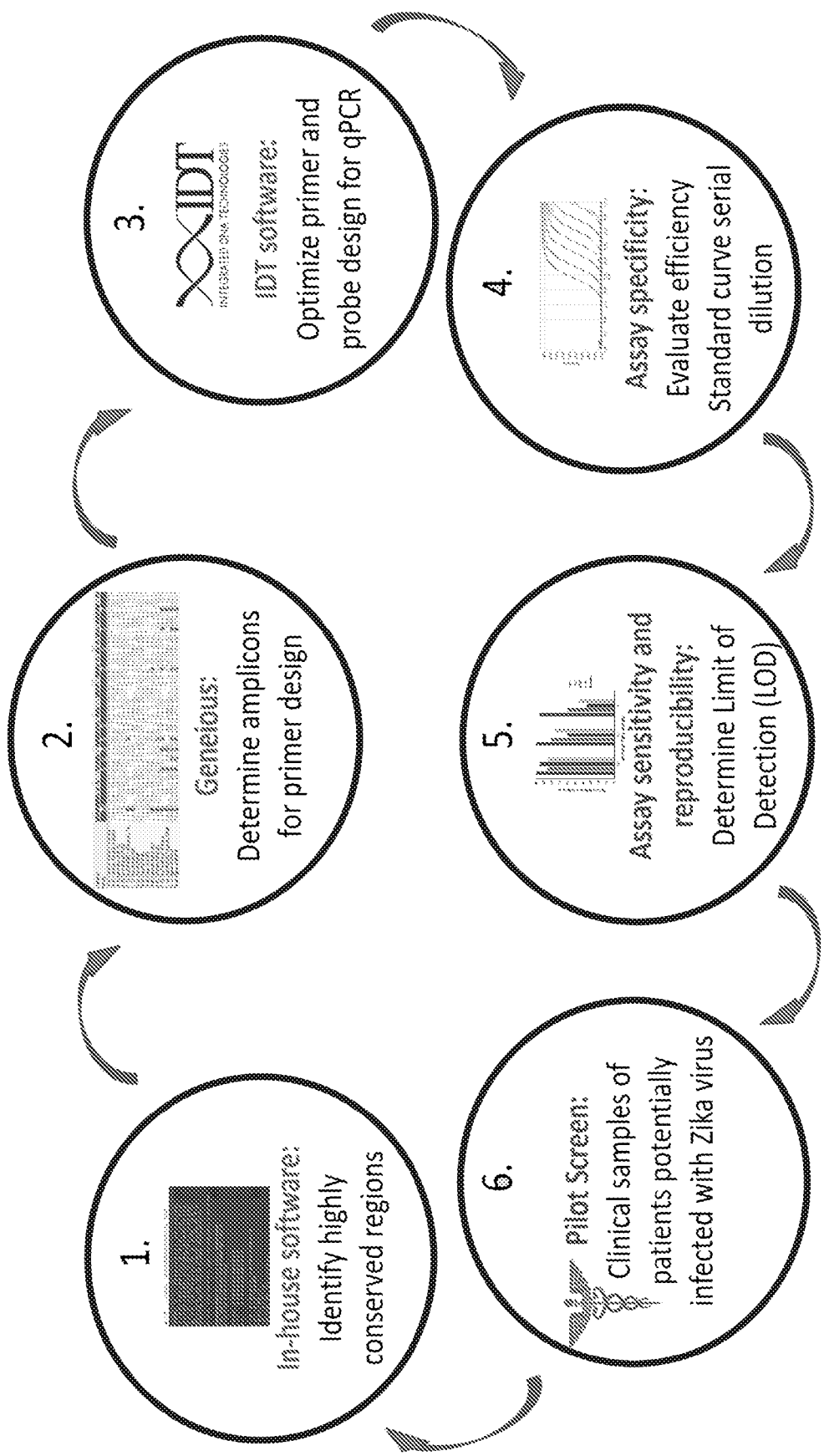
FIG. 9—Shows a workflow for RT-qPCR diagnostic development.
Figure 10:
FIG. 10—Shows design for new Zika RT-qPCR assays.
Figure 12:
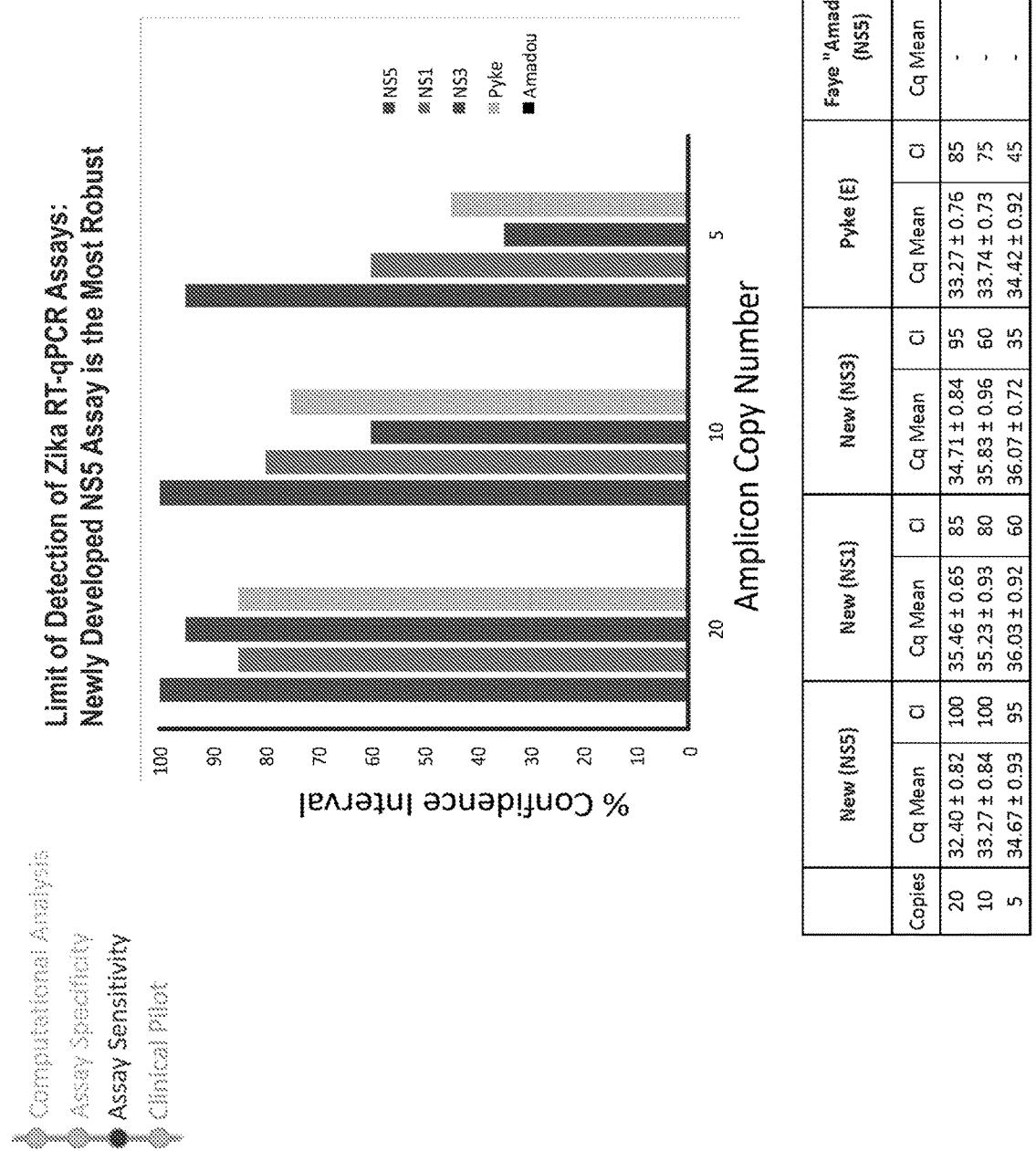
FIG. 12—Shows the limit of detection of Zika RT-qPCR assays. The NS5 assay was found to be the most robust.
Figure 14:
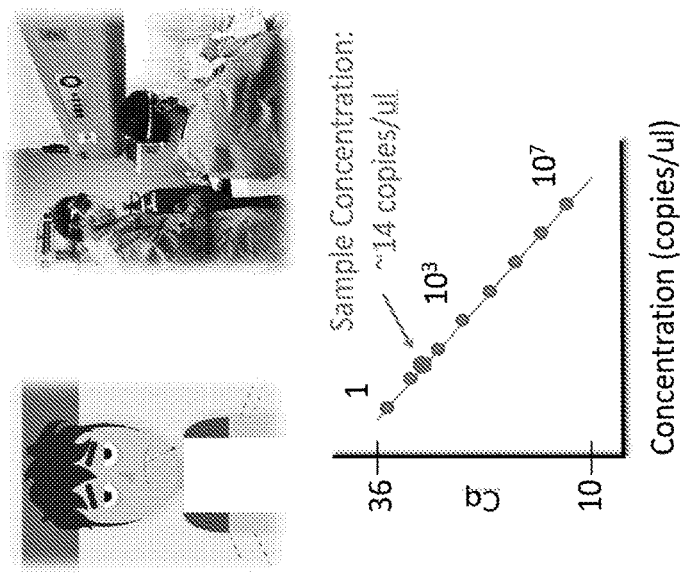
FIG. 14—Shows results of Zika NS5 probe-based diagnostic assay with concentration values.

Constructing the target sequence may comprise fragmenting the reference genomic sequences into fragments of equal size that overlap one another, so that the overlap between two fragments is half the size of the fragment, for example a 2× tiling as illustrated in FIG. 2.

As used herein, "individual hybridization pattern" is intended to designate the coverage capacity of one probe, i.e., the portion of the reference sequences to which the target sequence is capable of aligning or hybridizing to. More generally, when used with respect to a plurality of target sequences, "hybridization pattern" is intended to designate the collective coverage capacity of the plurality of target sequences, i.e. the collection of subsequences of the reference sequence which at least one of the target sequences of the plurality of target sequences is capable of hybridizing or aligning to or to which at least one of the target sequences is redundant once aligned to the reference genomic sequence.

A set cover solving process may be used to identify target sequences that are highly conserved among the input genomic sequences. A set cover solving process may refer to any process that approximates the solution to the set cover problem or a problem equivalent to the set cover problem (see, e.g., Introduction to Algorithms (mitpress.mit.edu/books/introduction-algorithms) and cc.gatech.edu/fac/Vijay.Vazirani/book.pdf). A set cover problem may be described as follows: given a set of elements $\{1, 2 \ldots i \ldots m\}$, called the universe U, and a collection S of n subsets whose union covers the universe, the set cover problem is to identify the smallest set of subsets whose union equals the universe.

As used herein, "reference genomic sequence" is intended to encompass the singular and the plural. As such, when referring to a reference sequence, the cases where more than one reference sequence is also contemplated. Preferably, the reference sequence is a plurality of reference sequences, the number of which may be over 30; 50; 70; 100; 200; 300; 500; 1,000 and above. In certain example embodiments, the reference sequence is a genomic sequence. In certain example embodiments, the reference sequence is a plurality of genomic sequences. In certain example embodiments, the reference sequence is a plurality of genomic sequences from the same species or viral strain. In certain other example embodiments, the reference sequence is a plurality of genomic sequences from different species or viral strains.

In one embodiment, the reference sequence may be a collection of genomes of one type of virus, wherein the genomes collectively form a universe of elements that are the nucleotides (position within the genomes being considered as differentiating nucleotides of the same type). In another embodiment, each genome may make up one universe so that the problem as a whole becomes a multi-universe problem. Multi-universe may be a unique generalization of the set cover problem. In this instance, separate universes may be helpful for thinking about partial set cover, so that this way, a partial cover yields a desired partial coverage of each genome (i.e., each universe). If the problem is imagined as being composed of a single universe, thinking about partial coverage may be considered as covering a desired fraction of the concatenation of all the genomes, rather than a desired fraction of each genome.

I If X designates a genome and y designates a position within the corresponding genome, an element of the universe can be represented by (X, y), which is understood as the nucleotide in position y in genome X. Candidate probes are obtaining by fragmenting the collection of genomes. The individual hybridization patterns are subsets of the universe. The individual hybridization pattern of a candidate probe of length L can be represented as $\{(A, ai), (A, ai+1) \ldots (A, ai+L), (A, aj), (A, aj+1) \ldots (A, aj+L), (B, bi), (B, bi+1) \ldots (B, bi+L) \ldots \}$, otherwise represented as $\{A:(ai \ldots ai+L), (aj \ldots aj+L); B:(b1 \ldots b1+L) \ldots \}$ (subset covering nucleotides in position ai to ai+L and aj to aj+L in genome A, nucleotides in position bi to bi+L in genome B . . . ).

In certain example embodiments, the target genomic sequences are viral genomic sequences. The viral sequences may be variants of the same viral strain, different viruses, or a combination thereof. A hybridization pattern is determined for the target sequences. To model a hybridization pattern, a number of different parameters may be defined to determine whether a given target sequence is considered to hybridize to a given portion of a reference genomic sequence. In addition, a percent of coverage parameter may be set to define the percent of the target sequence that should be covered by the probe set. This value may range from a fraction of a percent to 100% of the genome. In certain example embodiments, this may range from 0.01% to 10%, 1% to 5%, 1% to 10%, 1% to 15%, 1% to 20%, 1% to 25%, or the like.

In certain example embodiments, a number of mismatch parameters is defined. The number of mismatches defines a number of mismatches that may be present between a probe and a given portion of a target sequence. This value may range from 0 to 10 base pairs.

In certain example embodiments, another parameter, called the "island of exact match" substring, may be used to model hybridization between a probe and nucleic acid fragment. Let its value be x. When determining whether a probe covers a sequence, a value is set that defines a stretch of at least x bp in the probe that exactly matches (i.e., with no mismatches) a stretch of a target sequence. Along with the other parameters, this is applied as a filter to decide whether a probe should be deemed as hybridizing to a portion of a target sequence. The value may vary, but is usually set to be 30 bp. Setting its value to 0 would effectively remove this filter when determining hybridization patterns.

In certain other example embodiments, a longest common substring parameter may be set. This parameter defines that a probe only hybridizes if the longest common substring up to a certain amount of mismatches is at least that parameter. For example, if the parameter is set to 80 base pair with 3 mismatches, then a probe will still be considered to hybridized to a portion of a target sequence if there is string of 80 base pairs that match the target sequence, even if within that stretch, there are up to 3 mismatches. So, an 80-base-pair string that matches except for two mismatches would be considered to be hybridized, but an 80-base-pair string that matches except for 4 mismatches would not be considered to hybridize. This parameter may range from a string of 20 to 175 base pairs with anywhere from 0 to 9 mismatches in that string.

In certain other example embodiments, an overhang or cover extension parameter may be set. This parameter indicates that once a probe is found to hybridize, that probe will be considered to cover, or account for, X additional base pairs upstream and downstream of where the probe has bound. This parameter allows the number of total probes required to be reduced further because it will be understood that a probe, e.g., 100 base pairs, will not only account for the 100 base pairs portion it directly binds to, but may be reliably considered to capture a fragment that is at least 50 base pairs longer than the 100 base pair string. This parameter may vary between 0 and 200. In certain example embodiments, this parameter is set to 50.

This can be used, for example, in sequencing genomes of a virus for which a collection of genomes is available from previous studies, such as Zika virus. The collection of available genomes from previous studies is taken as reference target. One aim may be the study and monitoring of the evolution of the virus, for example throughout an outbreak, in order to determine proper actions to be taken for containing the outbreak and stopping it by sequencing regularly, if not systematically, the genome of the virus that infects a patient known to have contracted it.

The set cover solving process may be a weighted set cover solving process, i.e., each of the individual hybridization patterns is allocated a weight.

For example, a lower weight is allocated to those individual hybridization patterns that correspond to candidate target sequences that are specific to the reference sequence and a higher weight is allocated to those individual hybridization patterns that correspond to target sequences that are not specific to the reference sequence. Thus, the method may further comprise determining the specificity of each target sequence with regard to the reference sequence. For example, determining the stringency of hybridization may be indicative of the specificity of the target sequence. The higher weight is determined based on when a target sequence hybridizes to some other reference sequence (not a target). Another mismatch parameter may be utilized when assigning higher weights, which is usually a looser and more tolerant value. For example, there may be a mismatch parameter with a value of 3 for determining whether a target sequence hybridizes to a region of a reference sequence, but a separate tolerant mismatch parameter with a value of 10 for determining whether a probe hits a blacklisted sequence or more than one virus type in identification. The reason is desired increased sensitivity in determining these kinds of hits and more specificity in determining where target sequence cover reference sequences.

The weighted set cover solving process makes it possible to reduce substantially, if not dramatically, the number of selected target sequences that are highly conserved among reference sequences.

In certain example embodiments, the reference sequence forms a universe of elements that are the nucleotides (positions within the genomes being considered as differentiating nucleotides of the same type). If X designates the target sequence and y designates a position within the corresponding genome, an element of the universe can be represented by (X, y), which is understood as the nucleotide in position y in the target sequence X, or simply (y) because all y belongs to the same target sequence. Target sequences are obtained by fragmenting the reference sequence. It is then determined which target sequences are specific to the reference sequence and which are not. The individual hybridization patterns are subsets of the universe. The individual hybridization pattern of a target sequence of length L and which is specific to the reference sequence can be represented as (w, {(ai), (ai+1) . . . (ai+L), (aj), (aj+1) . . . (aj+L)}), otherwise represented as (w, {(ai . . . ai+L), (aj . . . aj+L)}) (subset covering nucleotides in position ai to ai+L . . . and aj to aj+L to which a weight w is given). The individual hybridization pattern of a target sequence of length L and which is not specific to the reference sequence would be represented in the same manner but will receive weight W instead, wherein W>w, preferably W>>w, more preferably W is infinity and w is 1.

If the reference sequence is a collection of reference sequences, then the individual hybridization pattern of a candidate probe of length L and which is specific to the reference sequence can be represented as (V, {(A, ai), (A, ai+1) . . . (A, ai+L), (A, aj), (A, aj+1) . . . (A, aj+L), (B, bi), (B, bi+1) . . . (B, bi+L) . . . }), otherwise represented as (V, {A:(ai . . . ai+L), (aj . . . aj+L); B:(bi . . . bi+L) . . . }) (subset covering nucleotides in position ai to ai+L and aj to aj+L in genome A, nucleotides in position bi to bi+L in genome B . . . to which a weight V is given).

Allocating the same weight to all the individual hybridization patterns amounts to an un-weighted set cover solving process, in other words, a set cover solving process without allocation of any weight, such as described above. Both weighted set cover solving process and un-weighted set cover solving process are contemplated by the invention.

A higher number of allowed mismatches for the weighted than for the un-weighted set cover solving process may be used, which is considered to be a separate, more tolerant parameter choice—in addition to the regular mismatch parameter that would be used (in the un-weighted problem) for determining hybridizations to target sequences. But, if the higher number does not replace the lower number, it is an additional parameter.

One example of a process that approximates the solution to the set cover problem is the greedy method. The greedy method is an iterative method wherein at each iteration, the solution that appears the best is chosen. When applied to the set cover problem at each iteration, the subset with the widest coverage of the yet uncovered universe is selected and the elements covered by the subset with the widest coverage are deleted from the yet uncovered universe. This is repeated until all the selected subsets collectively cover the entire universe, in other words, the yet uncovered universe, is empty.

Within the scope of the invention, this means that, at each iteration, the target sequence with the widest individual hybridization pattern within yet uncovered portions of the reference sequence is selected as one of the selected target sequences. The selection is repeated among the remaining target sequences until the selected probes collectively have a hybridization pattern that equals the desired coverage percentage of the reference sequences.

The method may further comprise minimizing a loss function depending on overhang parameters and mismatch parameters (or any parameters that alters the number of output probes) such that the total number of selected probes is no higher than a threshold number to provide input parameters to the set cover solving process. An overhang parameter ("cover extension") determines the number of nucleotides of one or both ends of a target sequence or a fragment thereof that remain unpaired once the target sequence or the fragment thereof hybridizes a selected probe. The higher the overhang parameter is, the lower the number of selected probes output by the set cover solving process. The value of the overhang parameters can range from 0 to 200 bp, and any sub-range therein. A mismatch parameter is the acceptable number of mismatches between a selected probe and the target sequence or the fragment thereof. The higher the mismatch parameter is, the lower the number of selected probes. In certain example embodiments, the mismatch parameter may have a range from 0 to 9.

In the case of a plurality of target sequence types, one overhang parameter and one mismatch parameter is assigned to each reference sequence or types thereof. The values of the overhang and mismatch parameters may be indicative of the diversity of the reference sequence, especially when selecting these parameters under the constraint of having a fixed number of probes.

The loss function is constructed so that the higher the value of the overhang parameter, the higher the value of the loss function, and the higher the value of the mismatch parameter, the higher the value of the loss function.

The use of a constraint while minimizing the loss function ensures that the number of selected probes remains lower than a reasonable amount, depending on the application of the selected probes.

The selected primers or probe can be used in a composition form, as part of a kit or a system for detection of pathogen nucleic acids sequence. The kit may comprise primers and/or probes generated from the identified target sequences, e.g., in a composition form, and a solid phase operably linked to the selected probes. The system may comprise the selected probes, i.e., in a composition form; a sample containing DNA of said target organism and the non-specific DNA; and a solid phase operably connected to the selected probes.

The solid phase may be a chip or beads. The selected probes may further comprise an adapter, for example a label. Each selected probe may comprise two adapters. Preferably, a first adapter is alternated with a second adapter.

As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences.

Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. % homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package, the default gap penalty for amino acid sequences is −12 for a gap and −4 for each extension. Calculation of maximum % homology, therefore, first requires the production of an optimal alignment, taking into consideration gap penalties. A suitable computer program for carrying out such an alignment is the GCG Wisconsin Bestfit package (Devereux et al., 1984 *Nuc. Acids Research* 12 p387). Examples of other software than may perform sequence comparisons include, but are not limited to, the BLAST package (see Ausubel et al., 1999 *Short Protocols in Molecular Biology*, 4th Ed. —Chapter 18), FASTA (Altschul et al., 1990 *J. Mol. Biol.* 403-410) and the GENEWORKS suite of comparison tools. Both BLAST and FASTA are available for offline and online searching (see Ausubel et al., 1999, *Short Protocols in Molecular Biology*, pages 7-58 to 7-60). However, for some applications, it is preferred to use the GCG Bestfit program. A new tool, called BLAST 2 Sequences is also available for comparing protein and nucleotide sequences (see *FEMS Microbiol Lett.* 1999 174(2): 247-50; *FEMS Microbiol Lett.* 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins DG & Sharp PM (1988), Gene 73(1), 237-244). Once the software has produced an optimal alignment, it is possible to calculate % homology, preferably % sequence identity. The software typically does this as part of the sequence comparison and generates a numerical result.

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids, such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as 0), pyridylalanine, thienylalanine, naphthylalanine and phenylglycine.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Hybridization can be performed under conditions of various stringency. Suitable hybridization conditions for the practice of the present invention are such that the recognition interaction between the probe and sequences associated with a signaling biochemical pathway is both sufficiently specific and sufficiently stable. Conditions that increase the stringency of a hybridization reaction are widely known and published in the art. See, for example, (Sambrook, et al., (1989); Nonradioactive In Situ Hybridization Application Manual, Boehringer Mannheim, second edition). The hybridization assay can be formed using probes immobilized on any solid support, including but are not limited to nitrocellulose, glass, silicon, and a variety of gene arrays. A preferred hybridization assay is conducted on high-density gene chips as described in U.S. Pat. No. 5,445,934.

For a convenient detection of the probe-target complexes formed during the hybridization assay, the nucleotide probes are conjugated to a detectable label. Detectable labels suitable for use in the present invention include any composition detectable by photochemical, biochemical, spectroscopic, immunochemical, electrical, optical or chemical means. A wide variety of appropriate detectable labels are known in the art, which include fluorescent or chemiluminescent labels, radioactive isotope labels, enzymatic or other ligands. In preferred embodiments, one will likely desire to employ a fluorescent label or an enzyme tag, such as digoxigenin, β-galactosidase, urease, alkaline phosphatase or peroxidase, avidin/biotin complex.

The detection methods used to detect or quantify the hybridization intensity will typically depend upon the label selected above. For example, radiolabels may be detected using photographic film or a phosphorimager. Fluorescent markers may be detected and quantified using a photodetector to detect emitted light. Enzymatic labels are typically detected by providing the enzyme with a substrate and measuring the reaction product produced by the action of the enzyme on the substrate; and finally colorimetric labels are detected by simply visualizing the colored label.

Examples of the labeling substance which may be employed include labeling substances known to those skilled in the art, such as fluorescent dyes, enzymes, coenzymes, chemiluminescent substances, and radioactive substances. Specific examples include radioisotopes (e.g., 32P, 14C, 125I, 3H, and 131I), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added.

Advantageously, the label is a fluorescent label. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcoumarin (Coumaran 151); cyanine dyes; cyanosine; 4',6-diamidino-2-phenylindole (DAPI); 5'5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolla Blue; phthalocyanine; and naphthalocyanine.

The fluorescent label may be a fluorescent protein, such as blue fluorescent protein, cyan fluorescent protein, green fluorescent protein, red fluorescent protein, yellow fluorescent protein or any photoconvertible protein. Colorimetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terylene. In the alternative, the fluorescent label may be a fluorescent bar code.

In an advantageous embodiment, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation.

In an advantageous embodiment, agents may be uniquely labeled in a dynamic manner (see, e.g., international patent application serial no. PCT/US2013/61182 filed Sep. 23, 2012). The unique labels are, at least in part, nucleic acid in nature, and may be generated by sequentially attaching two or more detectable oligonucleotide tags to each other and each unique label may be associated with a separate agent. A detectable oligonucleotide tag may be an oligonucleotide that may be detected by sequencing of its nucleotide sequence and/or by detecting non-nucleic acid detectable moieties to which it may be attached.

The oligonucleotide tags may be detectable by virtue of their nucleotide sequence, or by virtue of a non-nucleic acid detectable moiety that is attached to the oligonucleotide such as, but not limited to, a fluorophore, or by virtue of a combination of their nucleotide sequence and the non-nucleic acid detectable moiety.

In some embodiments, a detectable oligonucleotide tag may comprise one or more non-oligonucleotide detectable moieties. Examples of detectable moieties may include, but are not limited to, fluorophores, microparticles, including quantum dots (Empedocles, et al., Nature 399:126-130, 1999), gold nanoparticles (Reichert et al., Anal. Chem. 72:6025-6029, 2000), biotin, DNP (dinitrophenyl), fucose, digoxigenin, haptens, and other detectable moieties known to those skilled in the art. In some embodiments, the detectable moieties may be quantum dots. Methods for detecting such moieties are described herein and/or are known in the art.

Thus, detectable oligonucleotide tags may be, but are not limited to, oligonucleotides that may comprise unique nucleotide sequences, oligonucleotides that may comprise detectable moieties, and oligonucleotides that may comprise both unique nucleotide sequences and detectable moieties.

A unique label may be produced by sequentially attaching two or more detectable oligonucleotide tags to each other. The detectable tags may be present or provided in a plurality of detectable tags. The same or a different plurality of tags may be used as the source of each detectable tag may be part of a unique label. In other words, a plurality of tags may be subdivided into subsets and single subsets may be used as the source for each tag.

A unique nucleotide sequence may be a nucleotide sequence that is different (and thus distinguishable) from the sequence of each detectable oligonucleotide tag in a plurality of detectable oligonucleotide tags. A unique nucleotide sequence may also be a nucleotide sequence that is different (and thus distinguishable) from the sequence of each detectable oligonucleotide tag in a first plurality of detectable oligonucleotide tags but identical to the sequence of at least one detectable oligonucleotide tag in a second plurality of detectable oligonucleotide tags. A unique sequence may differ from other sequences by multiple bases (or base pairs). The multiple bases may be contiguous or non-contiguous. Methods for obtaining nucleotide sequences (e.g., sequencing methods) are described herein and/or are known in the art.

In some embodiments, detectable oligonucleotide tags comprise one or more of a ligation sequence, a priming sequence, a capture sequence, and a unique sequence (optionally referred to herein as an index sequence). A ligation sequence is a sequence complementary to a second nucleotide sequence which allows for ligation of the detectable oligonucleotide tag to another entity which may comprise the second nucleotide sequence, e.g., another detectable oligonucleotide tag or an oligonucleotide adapter. A priming sequence is a sequence complementary to a primer, e.g., an oligonucleotide primer used for an amplification reaction such as but not limited to PCR. A capture sequence is a sequence capable of being bound by a capture entity. A capture entity may be an oligonucleotide which may comprise a nucleotide sequence complementary to a capture sequence, e.g. a second detectable oligonucleotide tag. A capture entity may also be any other entity capable of binding to the capture sequence, e.g. an antibody, hapten, or peptide. An index sequence is a sequence that may comprise a unique nucleotide sequence and/or a detectable moiety as described above.

The present invention also relates to a computer system involved in carrying out the methods of the invention relating to both computations and sequencing.

A computer system (or digital device) may be used to receive, transmit, display and/or store results, analyze the results, and/or produce a report of the results and analysis. A computer system may be understood as a logical apparatus that can read instructions from media (e.g., software) and/or network port (e.g., from the internet), which can optionally be connected to a server having fixed media. A computer system may comprise one or more of a CPU, disk drives, input devices such as keyboard and/or mouse, and a display (e.g., a monitor). Data communication, such as transmission of instructions or reports, can be achieved through a communication medium to a server at a local or a remote location. The communication medium can include any means of transmitting and/or receiving data. For example, the communication medium can be a network connection, a wireless connection, or an internet connection. Such a connection can provide for communication over the World Wide Web. It is envisioned that data relating to the present invention can be transmitted over such networks or connections (or any other suitable means for transmitting information, including but not limited to mailing a physical report, such as a print-out) for reception and/or for review by a receiver. The receiver can be, but is not limited to an individual, or electronic system (e.g., one or more computers, and/or one or more servers).

In some embodiments, the computer system may comprise one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other suitable storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

A client-server, relational database architecture can be used in embodiments of the invention. A client-server architecture is a network architecture in which each computer or process on the network is either a client or a server. Server computers are typically powerful computers dedicated to managing disk drives (file servers), printers (print servers), or network traffic (network servers). Client computers include PCs (personal computers) or workstations on which users run applications, as well as example output devices as disclosed herein. Client computers rely on server computers for resources, such as files, devices, and even processing power. In some embodiments of the invention, the server computer handles all of the database functionality. The client computer can have software that handles all the front-end data management and can also receive data input from users.

A machine-readable medium which may comprise computer-executable code may take many forms, including, but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc., shown in the drawings. Volatile storage media include dynamic memory, such as main memory of such a computer platform. Tangible transmission media include coaxial cables, copper wire, and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include, for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The subject computer-executable code can be executed on any suitable device which may comprise a processor, including a server, a PC, or a mobile device such as a smartphone or tablet. Any controller or computer optionally includes a monitor, which can be a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard, mouse, or touch-sensitive screen, optionally provide for input from a user. The computer can include appropriate software for receiving user instructions, either in the form of user input into a set of parameter fields, e.g., in a GUI, or in the form of preprogrammed instructions, e.g., preprogrammed for a variety of different specific operations.

The present invention also contemplates multiplex assays. The present invention is especially well suited for multiplex assays. For example, the invention encompasses use of a SureSelectXT, SureSelectXT2 and SureSelectQXT Target Enrichment System for Illumina Multiplexed Sequencing developed by Agilent Technologies (see, e.g., agilent.com/genomics/protocolvideos), a SeqCap EZ kit developed by Roche NimbleGen, a TruSeq® Enrichment Kit developed by Illumina and other hybridization-based target enrichment methods and kits that add sample-specific sequence tags either before or after the enrichment step, as well as Illumina HiSeq, MiSeq and NexSeq, Life Technology Ion Torrent. Pacific Biosciences PacBio RSII, Oxford Nanopore MinIon, PromethIon and GridIon and other massively parallel Multiplexed Sequencing Platforms.

Microbe Detection

In some embodiments, the methods described herein may be used for detecting microbes, such as a virus or parasitic pathogen such as those described herein, in samples. Such detection may comprise providing a sample as described herein with reagents for detection, incubating the sample or set of samples under conditions sufficient to allow binding of the primers or probes to nucleic acid corresponding to one or more microbe-specific targets wherein a positive signal is generated; and detecting the positive signal, wherein detection of the detectable positive signal indicates the presence of one or more target molecules from a microbe, i.e., a virus, in the sample. The one or more target molecules may be any type of nucleic acid, including, but not limited to, mRNA, rRNA, tRNA, genomic DNA (coding or non-coding), or a combination of any of these, wherein the nucleic acid comprises a target nucleotide sequence that may be used to distinguish two or more microbial species/strains from one another.

The embodiments disclosed herein may also utilize certain steps to improve hybridization and/or amplification between primers and/or probes of the invention and target nucleic acid sequences. Methods for enhancing nucleic acid hybridization and/or amplification are well-known in the art. A viral- or microbe-specific target may be a nucleic acid such as RNA or DNA, or a target may be a protein, such as a viral- or microbe-encoded protein.

In some embodiments, hybridization between a primer and/or probe of the invention and a viral or microbial target sequence may be performed to verify the presence of the virus and/or microbe in the sample. In some specific cases, one or more viruses or microbes may be detected simultaneously. In other embodiments, a primer and/or probe of the invention may distinguish between 2 or more different viruses or microbes, even where those viruses and/or microbes may be sufficiently similar at the nucleotide level.

Detection of Single Nucleotide Variants

In some embodiments, one or more identified target sequences may be detected and/or differentiated using primers and/or probes of the invention that are specific for and bind to the target sequence as described herein. The systems and methods of the present invention can distinguish even between single nucleotide polymorphisms present among different viral or microbial species and therefore, use of multiple primers or probes in accordance with the invention may further expand on or improve the number of target sequences that may be used to distinguish between species. For example, in some embodiments, one or more primers and/or probes may distinguish between viruses and/or microbes at the species, genus, family, order, class, phylum, kingdom, or phenotype, or a combination thereof.

In certain example embodiments, a method or diagnostic test may be designed to screen viruses and/or microbes across multiple phylogenetic and/or phenotypic levels at the same time. For example, the method or diagnostic may comprise the use of multiple sets of primers and/or probes as described herein. Such an approach may be helpful for distinguishing viruses and/or microbes at the genus level, while further sets of primers/probes may distinguish at the species level. Thus, in accordance with the invention, a matrix may be produced identifying all viruses and/or microbes identified in a given sample. The foregoing is for example purposes only. Other means for classifying other microbe types are also contemplated and fall within the scope of the present invention so long as they find use of the primers and/or probes as described herein.

In certain other example embodiments, amplification of genetic material using a primer developed and/or described herein may be performed. Genetic material may comprise, for example, DNA and/or RNA, or a hybrid thereof, may be used to amplify the target nucleic acids. Amplification reactions employ recombinases, which are capable of pairing sequence-specific primers, such as described herein, with homologous sequence in the target nucleic acid, e.g., duplex DNA. If target DNA is present, DNA amplification is initiated and primers of the invention may anneal to the target sequence such that amplification of the target sequence may occur. Amplification reactions may be carried out at any appropriate temperature and using any reagents appropriate for the particular application or for the particular viral or microbial species. A primer of the invention is designed to amplify a sequence comprising the target nucleic acid sequence to be detected. In certain example embodiments, an RNA polymerase promoter, such as a T7 promoter, may be added to one of the primers, to result in an amplified double-stranded DNA product comprising the target sequence and an RNA polymerase promoter. After, or during, the amplification reaction, an RNA polymerase may be added that will produce RNA from the double-stranded DNA template. The amplified target RNA can then be detected as described herein. In this way, target DNA may be detected using the embodiments disclosed herein. Amplification reactions may also be used to amplify target RNA. The target RNA is first converted to cDNA using a reverse transcriptase reaction, followed by second strand DNA synthesis, at which point the amplification reaction proceeds as outlined above.

Accordingly, in certain example embodiments the systems disclosed herein may include amplification reagents. Different components or reagents useful for amplification of nucleic acids are described herein. For example, an amplification reagent as described herein may include a buffer, such as a Tris buffer. A Tris buffer may be used at any concentration appropriate for the desired application or use, for example including, but not limited to, a concentration of 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 25 mM, 50 mM, 75 mM, 1 M, or the like. One of skill in the art will be able to determine an appropriate concentration of a buffer such as Tris for use with the present invention.

A salt, such as magnesium chloride ($MgCl_2$), potassium chloride (KCl), or sodium chloride (NaCl), may be included in an amplification reaction, such as PCR, in order to improve the amplification of nucleic acid fragments. Although the salt concentration will depend on the particular reaction and application, in some embodiments, nucleic acid fragments of a particular size may produce optimum results at particular salt concentrations. Larger products may require altered salt concentrations, typically lower salt, in order to produce desired results, while amplification of smaller products may produce better results at higher salt concentrations. One of skill in the art will understand that the presence and/or concentration of a salt, along with alteration of salt concentrations, may alter the stringency of a biological or chemical reaction, and therefore any salt may be used that provides the appropriate conditions for a reaction of the present invention and as described herein.

Other components of a biological or chemical reaction may include a cell lysis component in order to break open or lyse a cell for analysis of the materials therein. A cell lysis component may include, but is not limited to, a detergent, a salt as described above, such as NaCl, KCl, ammonium sulfate [$(NH_4)_2SO_4$], or others. Detergents that may be appropriate for the invention may include Triton X-100, sodium dodecyl sulfate (SDS), CHAPS (3-[(3-cholamidopropyl)dimethylammonio]-1-propanesulfonate), ethyl trimethyl ammonium bromide, nonyl phenoxypolyethoxylethanol (NP-40). Concentrations of detergents may depend on the particular application, and may be specific to the reaction in some cases. Amplification reactions may include dNTPs and nucleic acid primers used at any concentration appropriate for the invention, such as including, but not limited to, a concentration of 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 1 mM, 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, 100 mM, 150 mM, 200 mM, 250 mM, 300 mM, 350 mM, 400 mM, 450 mM, 500 mM, or the like. Likewise, a polymerase useful in accordance with the invention may be any specific or general polymerase known in the art and useful or the invention, including Taq polymerase, Q5 polymerase, or the like.

In some embodiments, amplification reagents as described herein may be appropriate for use in hot-start amplification. Hot start amplification may be beneficial in some embodiments to reduce or eliminate dimerization of oligos, or to otherwise prevent unwanted amplification products or artifacts and obtain optimum amplification of the desired product. Many components described herein for use in amplification may also be used in hot-start amplification. In some embodiments, reagents or components appropriate for use with hot-start amplification may be used in place of one or more of the composition components as appropriate. For example, a polymerase or other reagent may be used that exhibits a desired activity at a particular temperature or other reaction condition. In some embodiments, reagents may be used that are designed or optimized for use in hot-start amplification, for example, a polymerase may be activated after transposition or after reaching a particular temperature. Such polymerases may be antibody-based or aptamer-based. Polymerases as described herein are known in the art. Examples of such reagents may include, but are not limited to, hot-start polymerases, hot-start dNTPs, and photo-caged dNTPs. Such reagents are known and available in the art. One of skill in the art will be able to determine the optimum temperatures as appropriate for individual reagents.

Amplification of nucleic acids may be performed using specific thermal cycle machinery or equipment, and may be performed in single reactions or in bulk, such that any desired number of reactions may be performed simultaneously. In some embodiments, amplification may be performed using microfluidic or robotic devices, or may be performed using manual alteration in temperatures to achieve the desired amplification. In some embodiments, optimization may be performed to obtain the optimum reactions conditions for the particular application or materials. One of skill in the art will understand and be able to optimize reaction conditions to obtain sufficient amplification.

In certain embodiments, detection of DNA with the methods or systems of the invention requires transcription of the (amplified) DNA into RNA prior to detection.

Set Cover Approaches

In particular embodiments, a primer and/or probe is designed that can identify, for example, all viral and/or microbial species within a defined set of viruses and microbes. Such methods are described in certain example embodiments. A set cover solution may identify the minimal number of target sequence probes or primers needed to cover an entire target sequence or set of target sequences, e.g. a set of genomic sequences. Set cover approaches have been used previously to identify primers and/or microarray probes, typically in the 20 to 50 base pair range. See, e.g. Pearson et al., cs.virginia.edu/~robins/papers/primers_dam11_final.pdf., Jabado et al. Nucleic Acids Res. 2006 34(22):6605-11, Jabado et al. Nucleic Acids Res. 2008, 36(1):e3 doi10.1093/nar/gkm1106, Duitama et al. Nucleic Acids Res. 2009, 37(8):2483-2492, Phillippy et al. *BMC Bioinformatics*. 2009, 10:293 doi:10.1186/1471-2105-10-293. Such approaches generally involved treating each primer/probe as k-mers and searching for exact matches or allowing for inexact matches using suffix arrays. In addition, the methods generally take a binary approach to detecting hybridization by selecting primers or probes such that each input sequence only needs to be bound by one primer or probe and the position of this binding along the sequence is irrelevant. Alternative methods may divide a target genome into pre-defined windows and effectively treat each window as a separate input sequence under the binary approach—i.e. they determine whether a given probe or guide RNA binds within each window and require that all of the windows be bound by the state of some primer or probe. Effectively, these approaches treat each element of the "universe" in the set cover problem as being either an entire input sequence or a pre-defined window of an input sequence, and each element is considered "covered" if the start of a probe or guide RNA binds within the element.

In some embodiments, the methods disclosed herein may be used to identify all variants of a given virus, or multiple different viruses in a single assay. Further, the method disclosed herein treat each element of the "universe" in the set cover problem as being a nucleotide of a target sequence, and each element is considered "covered" as long as a probe or guide RNA binds to some segment of a target genome that includes the element. Rather than only asking if a given primer or probe does or does not bind to a given window, such approaches may be used to detect a hybridization pattern—i.e. where a given primer or probe binds to a target sequence or target sequences—and then determines from those hybridization patterns the minimum number of primers or probes needed to cover the set of target sequences to a degree sufficient to enable both enrichment from a sample and sequencing of any and all target sequences. These hybridization patterns may be determined by defining certain parameters that minimize a loss function, thereby enabling identification of minimal probe or guide RNA sets in a way that allows parameters to vary for each species, e.g. to reflect the diversity of each species, as well as in a computationally efficient manner that cannot be achieved using a straightforward application of a set cover solution, such as those previously applied in the primer or probe design context.

The ability to detect multiple transcript abundances may allow for the generation of unique viral or microbial signatures indicative of a particular phenotype. Various machine learning techniques may be used to derive the gene signatures. Accordingly, the primers and/or probes of the invention may be used to identify and/or quantitate relative levels of biomarkers defined by the gene signature in order to detect certain phenotypes. In certain example embodiments, the gene signature indicates susceptibility to a particular treatment, resistance to a treatment, or a combination thereof.

In one aspect of the invention, a method comprises detecting one or more pathogens. In this manner, differentiation between infection of a subject by individual microbes may be obtained. In some embodiments, such differentiation may enable detection or diagnosis by a clinician of specific diseases, for example, different variants of a disease. Preferably the viral or pathogen sequence is a genome of the virus or pathogen or a fragment thereof. The method further may comprise determining the evolution of the pathogen. Determining the evolution of the pathogen may comprise identification of pathogen mutations, e.g. nucleotide deletion, nucleotide insertion, nucleotide substitution. Among the latter, there are non-synonymous, synonymous, and noncoding substitutions. Mutations are more frequently non-synonymous during an outbreak. The method may further comprise determining the substitution rate between two pathogen sequences analyzed as described above. Whether the mutations are deleterious or even adaptive would require functional analysis, however, the rate of non-synonymous mutations suggests that continued progression of this epidemic could afford an opportunity for pathogen adaptation, underscoring the need for rapid containment. Thus, the method may further comprise assessing the risk of viral adaptation, wherein the number non-synonymous mutations is determined. (Gire, et al., *Science* 345, 1369, 2014).

Screening Environmental Samples

The methods disclosed herein may also be used to screen environmental samples for contaminants by detecting the presence of target nucleic acids or polypeptides. For example, in some embodiments, the invention provides a method of detecting viruses and/or microbes, comprising: exposing a primer and/or probe as described herein to a sample; allowing binding of the primer and/or probe to one or more viral- or microbe-specific target nucleic acids such that a detectable positive signal is produced. The positive signal can be detected and is indicative of the presence of one or more viruses or microbes in the sample.

As described herein, an environmental sample for use with the invention may be a biological or environmental sample, such as a food sample (fresh fruits or vegetables, meats), a beverage sample, a paper surface, a fabric surface, a metal surface, a wood surface, a plastic surface, a soil sample, a freshwater sample, a wastewater sample, a saline water sample, exposure to atmospheric air or other gas sample, or a combination thereof. For example, household/commercial/industrial surfaces made of any materials including, but not limited to, metal, wood, plastic, rubber, or the like, may be swabbed and tested for the presence of viruses and/or microbes. Soil samples may be tested for the presence of pathogenic viruses or bacteria or other microbes, both for environmental purposes and/or for human, animal, or plant disease testing. Water samples such as freshwater samples, wastewater samples, or saline water samples can be evaluated for cleanliness and safety, and/or potability, to detect the presence of a viral or microbial contaminant such as, for example, *Cryptosporidium parvum*, *Giardia lamblia*, or other microbial contamination. In further embodiments, a biological sample may be obtained from a source including, but not limited to, a tissue sample, saliva, blood, plasma, sera, stool, urine, sputum, mucous, lymph, synovial fluid, cerebrospinal fluid, ascites, pleural effusion, seroma, pus, or swab of skin or a mucosal membrane surface, or any other types of samples described herein above. In some particular embodiments, an environmental sample or biological samples may be crude samples and/or the one or more target molecules may not be purified or amplified from the sample prior to application of the method. Identification of microbes may be useful and/or needed for any number of applications, and thus any type of sample from any source deemed appropriate by one of skill in the art may be used in accordance with the invention.

A microbe in accordance with the invention may be a pathogenic virus or microbe or a microbe that results in food or consumable product spoilage. A pathogenic microbe may be pathogenic or otherwise undesirable to humans, animals, or plants. For human or animal purposes, a microbe may cause a disease or result in illness. Animal or veterinary applications of the present invention may identify animals infected with a microbe. For example, the methods and systems of the invention may identify companion animals with pathogens including, but not limited to, kennel cough, rabies virus, and heartworms. In other embodiments, the methods and systems of the invention may be used for parentage testing for breeding purposes. A plant microbe may result in harm or disease to a plant, reduction in yield, or alter traits such as color, taste, consistency, odor, For food or consumable contamination purposes, a microbe may adversely affect the taste, odor, color, consistency or other commercial properties of the food or consumable product. In certain example embodiments, the microbe is a bacterial species. The bacteria may be a psychrotroph, a coliform, a lactic acid bacteria, or a spore-forming bacteria. In certain example embodiments, the bacteria may be any bacterial species that causes disease or illness, or otherwise results in an unwanted product or trait. Bacteria in accordance with the invention may be pathogenic to humans, animals, or plants.

Table 1 provides a set of example primers and probes designed using the methods disclosed herein. Candidate target sequences (amplicons) and corresponding primers and probes were designed by applying the methods disclosed herein either to publicly available genomic sequences and/or clinical isolates of the target pathogen. The primer and probes in Table 1 may be used alone or in combination to screen or detect for multiple pathogens or variants within a sample.

TABLE 1

Sequences for Identification of Microbe

| qPCR Assay | Assay Forward Primer | Assay Reverse Primer | Assay PCR-Probe | Amplicon (Target Sequence) |
|---|---|---|---|---|
| Ebola | AATCGAGC GCAAGGTT ACA (Seq. I.D. No. 1) | CTTGCTTGGT GTCTGGAGT AT (Seq. I.D. No. 2) | AGGTTGAACTGAG AGTGTCTAGACAAC A (Seq. I.D. No. 3) | AATCGAGCGCAAGGTTACAA GGTTGAACTGAGAGTGTCTA GACAACAAAATATCGATACT CCAGACACCAAGCAAG (Seq. I.D. No. 4) |
| Zika | GGC TTG AAG CAA GAA TGC TC (Seq. ID. No. 5) | CCCTCAATG GCTGCTACTT T (Seq. I.D. No. 6) | AGATGGCCTC ATAGCCTCG CTCTA (Seq. I.D. No. 7) | GGCTTGAAGCAAGAATGCTC CTTGACAATATTTACCTCCAA GATGGCCTCATAGCCTCGCT CTATCGACCTGAGGCCGACA AAGTAGCAGCCATTGAGGG (Seq. I.D. No. 8) |
| Zika | ATTGAGGA A TGGTGCTG T AGG (Seq. I.D. No. 9) | GTTCTTTCCT GGGCCTTATC T (Seq. I.D. No. 10) | AAGACGGCTG CTGGTATGG AATGG (Seq. I.D. No. 11) | ATTGAGGAATGGTGCTGTAG GGAATGCACAATGCCCCCAC TATCGTTTCGAGCAAAAGAC GGCTGCTGGTATGGAATGGA GATAAGGCCCAGGAAAGAA C (Seq. I.D. No. 12) |

TABLE 1-continued

Sequences for Identification of Microbe

| qPCR Assay | Assay Forward Primer | Assay Reverse Primer | Assay PCR-Probe | Amplicon (Target Sequence) |
|---|---|---|---|---|
| Zika | TCATGAAGAACCCRTGYTGG (Seq. I.D. No. 13) | CTCAGCCGCCATRTGRAAGA (Seq. I.D. No. 14) | TGCAAAGCTATGGGTGGAACA (Seq. I.D. No. 15) | TCATGAAGAACCCGTGTTGGTGCAAAGCTATGGGTGGAACATAGTCCGTCTTAAGAGTGGGGTGGACGTCTTTCATATGGCGGCTGAG (Seq. I.D. No. 16) |
| Zika | AGYYGAYTGGGTHCCAAC TG (Seq. I.D. No. 17) | YTCCTCAATCCACACTCTRTTC (Seq. I.D. No. 18) | ACCTGGTCAATCCATGGAAAGGGA (Seq. I.D. No. 19) | AGTTGACTGGGTTCCAACTGGGAGAACTACCTGGTCAATCCATGGAAAGGGAGAATGGATGACCACTGAAGACATGCTTGTGGTGTGGAACAGAGTGTGGATTGAGGAG (Seq. I.D. No. 20) |
| Zika | CCAYTTCAACAARCTSYAYCT (SEQ. I.D. No. 21) | TTTGCWARCARGCAGTCTC (SEQ. I.D. No. 22) | TGCCGCCACCAAGATGAACTGA (SEQ. I.D. No. 23) | CCACTTCAACAAGCTCCATCTCAAGGACGGGAGGTCCATTGTGGTTCCCTGCCGCCACCAAGATGAACTGATTGGCCGGGCCCGCGTCTCTCCAGGGGCGGGATGGAGCATCCGGGAGACTGCTTGCCTAGCAAA (SEQ. I.D. No. 24) |
| Zika | TSYAGGGARTGCACAAT (SEQ. I.D. No. 25) | ACTAAGTTRCTYTCTGGTTCYTTY (SEQ. I.D. No. 26) | TGGTATGGAATGGAGATAAGGCCC (SEQ. I.D. No. 27) | AGGGAGTGCACAATGCCCCCACTGTCGTTCCGGGCTAAAGATGCTGTTGGTATGGAATGGAGATAAGGCCCAGGAAAGAACCAGAAAGCAACTTAGTAAGG (SEQ. I.D. No. 28) |
| Zika | AGAGACCCTGGGAGAGAAAT (SEQ. I.D. No. 29) | CTCGGTGATGCCTGACTTT (SEQ. I.D. No. 30) | AGATGTCGGCCCTGGAGTTCTACT (SEQ. I.D. No. 31) | AGAGACCCTGGGAGAGAAATGGAAGGCCCGCTTGAACCAGATGTCGGCCCTGGAGTTCTACTCCTACAAAAAGTCAGGCATCACCGAG (SEQ. I.D. No. 32) |
| Chikungunya | TTTGCAAGCTCCAGATCCA (SEQ. I.D. No. 33) | GTAGCTGTAGTGCGTACCTATTT (SEQ. I.D. No. 34) | GAGAAGCTCAGAGGACCCGT (SEQ. I.D. No. 35) | TTTGCAAGCTCCAGATCCAACTTCGAGAAGCTCAGAGGACCCGTCATAACTTTGTACGGCGGTCCTAAATAGGTACGCACTACAGCTAC (SEQ. I.D. No. 36) |
| Chikungunya | CGTTCTCGCATCTAGCCATAA (SEQ. I.D. No. 37) | TGATCCCGACTCAACCATCCTGG (SEQ. I.D. No. 38) | GTACTTCCTGTCCGACATCATC (SEQ. I.D. No. 39) | CGTTCTCGCATCTAGCCATAAAACTAATAGAGCAGGAAATTGATCCCGACTCAACCATCCTGGATATAGGTAGTGCGCCAGCAAGGAGGATGATGTCGGACAGGAAGTAC (SEQ. I.D. No. 40) |
| Chikungunya | CCCGACTCAACCATCCTG (SEQ. I.D. No. 41) | GCAGACGCAGTGGTACTT (SEQ. I.D. No. 42) | CCAGCAAGG AGGATGATGTCGG (SEQ. I.D. No. 43) | CCCCGACTCAACCATCCTGGATATCGGCAGTGCGCCAGCAAGGAGGATGATGTCGGACAGGAAGTACCAGGAAGTACCACTGCGTCTGCC (SEQ. I.D. No. 44) |
| Dengue | AACCWACGRAARAAGRCGV (SEQ. I.D. No. 45) | GRGAAWCTCTTYGYYARCTG (SEQ. I.D. No. 46) | TCAATATGCTGAAACGC (SEQ. I.D. No. 47) | AACCTACGAAAAAGACGGCTCGACCGTCTTTCAATATGCTGAAACGCGCGAGAAACCGCGTGTCAACTGTTTCACAGTTGGCGAAGAGATTCTC (SEQ. I.D. No. 48) |
| Babesia microti | CCTAGGTATGTATCATCTTAACCTCTTT (SEQ. I.D. No. 49) | TAGGGATCGTAGTCGTGTACTG (SEQ. I.D. No. 50) | CCCAAGTAGGTATCTATGTACTTCTACTG T (SEQ. I.D No 51) | GTTACCTAGGTATGTATCATCTTAACCTCTTACTACCCAAGTAGGTATCTATGTACTTCTACTGTACCTACTAATAGGACAAACAAGTGTAACTTGTAGCAGTACACGACTACGATCCCTATAG (SEQ. I.D. No. 52) |

TABLE 1-continued

Sequences for Identification of Microbe

| qPCR Assay | Assay Forward Primer | Assay Reverse Primer | Assay PCR-Probe | Amplicon (Target Sequence) |
|---|---|---|---|---|
| Lassa SL: (Specific to detect viral strains originating in Sierra Leone) | TCTCTGAC ATCTGTCT CGCA (SEQ. I.D. No. 53) | GTTGCAGCA GCTCTTCAC AAT (SEQ. I.D. No. 54) | N/A | CGAAGTGCGTCTAGTCCTTG TATCCAAGGCAAATCTACCC AGTCTCTGACATCTGTCTCG CAATTCAATAAGAATGGGTC AATAGGGTATCTTGCATATTG CAAAAGACTTAAGGTTCTTT TCTGTATTAGATTGCACAGGT GAACAGGGACACCATTCGC AACCGACTGATCAATGATTG TGTCAATTGTTTCTGCCAGTT GGTGTGGCTCTTTACACTTTA TATTGTGAAGAGCTGCTGCA ACGAACTTTGTCTAAGCAAG AGTCTGCGACTCCTGTGGAT CTAC (SEQ. I.D. No. 55) |
| Lassa NG: (Specific to detect viral strains originating in Nigeria) | YACAGGGT CYTCTGGW CGACC (SEQ. I.D. No. 56) | RATGATGCA RCTTGACCC AAG (SEQ. I.D. No. 57) | N/A | GCCCGACATAGGTTGGTAAA GAGCTATTTCCACAGGGTCT TCTGGACGACCTTCAATGTC TATCCAGGTTTTGGCACTTG GGTCAAGCTGCATCATTGAG TCTTTAAGTGTCATCAACTG AGAATAG (SEQ. I.D. No. 58) |

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

We claim:

1. A method for detecting Ebolavirus in samples, comprising:
   contacting a sample with a forward primer, a reverse primer, and a probe with a detectable label, wherein the forward primer is SEQ ID NO: 1, the reverse primer is SEQ ID NO: 2, and the probe with the detectable label is SEQ ID NO: 3; and
   detecting amplification of one or more target sequences by quantitative PCR using the forward primer, reverse primer, and the probe with the detectable label; wherein detection of the one or more target sequences indicates the presence of Ebolavirus.

* * * * *